US008288528B2

(12) United States Patent
Roncucci et al.

(10) Patent No.: US 8,288,528 B2
(45) Date of Patent: Oct. 16, 2012

(54) MESO-SUBSTITUTED PORPHYRINS

(75) Inventors: Gabrio Roncucci, Colle Val d'Elsa (IT); Donata Dei, San Gimignano (IT); Francesca Giuntini, Mercatale Val Di Pesa (IT); Giacomo Chiti, Montemurlo (IT); Daniele Nistri, Prato (IT); Lia Fantetti, Florence (IT); Valentina Paschetta, Greve In Chianti (IT); Annalisa Cocchi, Poggio a Caiano (IT)

(73) Assignee: L. Molteni & C. Dei Fratelli Alitti—Società di Esercizio S.p.A., Scandicci (IT)

( * ) Notice: Subject to any disclaimer, the term of this patent is extended or adjusted under 35 U.S.C. 154(b) by 0 days.

(21) Appl. No.: 13/007,345

(22) Filed: Jan. 14, 2011

(65) Prior Publication Data

US 2011/0112464 A1    May 12, 2011

Related U.S. Application Data

(63) Continuation of application No. 10/532,278, filed as application No. PCT/EP03/11642 on Oct. 21, 2003, now Pat. No. 7,947,674.

(30) Foreign Application Priority Data

Oct. 21, 2002    (IT) .................... FI2002A0200

(51) Int. Cl.
*C07B 47/00*    (2006.01)
(52) U.S. Cl. ...................................... 540/145
(58) Field of Classification Search ............ 540/145; 514/415
See application file for complete search history.

(56) References Cited

U.S. PATENT DOCUMENTS

| 5,965,598 A | 10/1999 | Roncucci et al. |
| 7,947,674 B2 | 5/2011 | Roncucci et al. |

FOREIGN PATENT DOCUMENTS

| EP | 0 906 758 | 4/1999 |
| WO | WO 98/33503 | 8/1998 |
| WO | WO 01/96343 | 12/2001 |
| WO | WO 02/10173 | 2/2002 |
| WO | WO 02/090361 | 11/2002 |

OTHER PUBLICATIONS

D. L. Dick, et al., "Molecular Encapsulation: Cyclodextrin-Based Analogues of Heme-Containing Proteins," *Journal of the American Chemical Society*, vol. 114, pp. 2664-2669 (1992).
Ito, et al., "Magnetic Field Effects on the Lifetimes of Triplet Biradicals Photogenerated from Zinc(II) Tetraphenylporphyrin-Viologen Chain-Linked Compounds: Dependence on Spacer Chain Length and Environment," *Bulletin of the Chemical Society of Japan*, vol. 74, pp. 657-665 (2001).
Jori, Giulio, "Tumour Photosensitizers: Approaches to Enhance the Selectivity and Efficiency of Photodynamic Therapy," *Journal of Photochemistry and Photobiology*, vol. 36, pp. 87-93 (1996).
Li, Tao, et al., "Preliminary Communication Magnetic-Field-Induced Fréedericksz Transition of a Planar Aligned Liquid Crystal Doped with Porphyrinatoiinc (II): Influence of the Substituent of the Porphyrin Ring," *Liquid Crystals*, vol. 27, pp. 551-553 (2000).
Merchat, Michele, et al., "Meso-Substituted Cationic Porphyrins as Efficient Photosensitizers of Gram-Positive and Gram-Negative Bacteria," *Journal of Photochemistry and Photobiology*, vol. 32, pp. 153-157 (1996).
Merchat, M., et al., "Studies on the Mechanism of Bacteria Photosensitization by Meso-Substituted Cationic Porphyrins," *Journal of Photochemistry and Photobiology*, vol. 35, pp. 149-157 (1996).
International Search Report for Application No. PCT/EP03/11642 mailed Jun. 2, 2004.
International Preliminary Examination Report for Application No. PCT/EP03/11642 mailed Jan. 21, 2005.

*Primary Examiner* — Paul V. Ward
(74) *Attorney, Agent, or Firm* — Wolf, Greenfield & Sacks, P.C.

(57) ABSTRACT

Meso-substituted porphyrins of general formula (I)

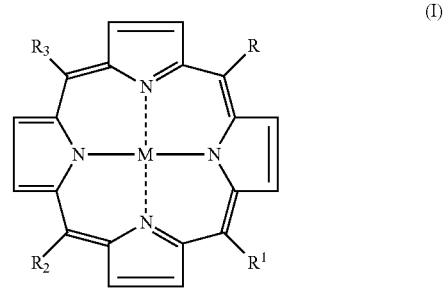

suitable for the use as photosensitizing agents, in particular in photodynamic therapy, are herein described.

10 Claims, No Drawings

MESO-SUBSTITUTED PORPHYRINS

RELATED APPLICATIONS

This application is a continuation of U.S. application Ser. No. 10/532,278, which entered the national stage on Apr. 21, 2005 and issued as U.S. Pat. No. 7,947,674 on May 24, 2011. U.S. application Ser. No. 10/532,278 is the national stage filing under 35 U.S.C. §371 of PCT International Application No. PCT/EP2003/11642, filed Oct. 21, 2003, which was published under PCT Article 21(2) in English. Each of the above applications is incorporated herein by reference.

FIELD OF THE INVENTION

The present invention refers to meso-substituted porphyrins of formula (I) hereinafter reported, the processes related to their preparation and use as photosensitising agents for therapeutic, diagnostic and photosterilisation uses.

STATE OF THE ART

It is known that tetrapyrrolic macrocycles, like porphyrins or other photosensitisers, are able to preferentially localise in neoplastic tissues and, once photo-activated by irradiation with visible light, they are capable of generating hyper-reactive derivatives of oxygen such as radicals and singlet-oxygen. Due to their high intrinsic reactivity, these species trigger irreversible oxidative cytotoxyc processes against cells and tissues, thus being highly cytotoxic after the localisation of the photosensitiser onto targets and irradiation.

Thanks to their properties, porphyrins are used as photosensitizers for the treatment of tumours in the so-called "photodynamic therapy" (hereinafter referred to as PDT).

A typical PDT protocol is based on the administration of an appropriate dose of photosensitizer, followed by irradiation of the tissues wherein the tumour is localised by using light of appropriate wavelength, thus causing, by the so-called photodynamic effect, the preferential or selective elimination of the tumour mass. Due to the selective localisation in tumour tissues these photosensitizers can therefore be used not only for therapeutic purposes, but also as diagnostic agents as their high fluorescence quantum yield allow the direct visualisation of the tumour lesion.

Besides in the photoinactivation of tumour cells, it has been shown that photosensitizers can also be used in the treatment and diagnosis of pre-tumour pathologies and for various hyperproliferative diseases like psoriasis, actinic keratosis, atheromas, endoarterial hyperplasia and prostate hyperplasia, as well as for microbial photoinactivation and therefore in the treatment of bacterial and micotic infections.

Although the early use of phorphyrins in PDT has given encouraging results, the compounds prepared until now need further improvements because of their markedly limited efficiency and poor selectivity toward the eukaryotic cells and/or micro-organisms, and because of the prolonged persistence in the skin, which often may cause phenomena of generalised photosensitivity (Jori G., *J. Photochem. Photobiol., B: Biol.*, Vol. 36, pp. 87-93, 1996).

Thus it is evident how important it is to develop novel porphyrin compounds suitable for the use as therapeutic agents in PDT and as diagnostic agents, but not showing the limitations illustrated above.

Some substituted porphyrins and metalloporphyrins are disclosed in Dick D. L. et al. *J. Am. Chem. Soc.* 114 (1992) 2664-2669. Their encapsulation within the hydrophobic cavity of cyclodextrins is reported, providing inclusion complexes capable of mimicking the activities of heme-containing proteins.

Porphyrin derivatives bearing cationic groups have been previously described (Merchat et al. *J. Photochem. Photobiol.* 32, 153-157, 1996; Merchat et al. *J. Photochem. Photobiol.* 35, 149-157, 1996) and assessed for their photodynamic properties in the bacteria photoinactivation. These compounds bear trimethyl-anilinium groups or quaternary ammonium pyridinium groups in the meso-positions and therefore are endowed by a hydrophilic nature.

Other photosensitisers such as phthalocyanines having hydrophilic and/or amphiphilic characteristics are known; for example, the International Applications No. WO 01/96343 and WO 02/090361, and in the U.S. Pat. No. 5,965,598, all in the name of the Applicant, disclose various evenly substituted hydrophilic phthalocyanines, as well as non centrosymmetrical phthalocyanines bearing cationic or protonable group on the macrocycle.

SUMMARY OF THE INVENTION

The Applicant has now found a novel series of photosensitizers having particularly advantageous properties compared to the known compounds.

These novel compounds have shown optimum physical-chemical features for therapeutic applications, particularly in relation to their absorption in the region of the visible spectrum, high molar extinction coefficients, high quantum yield in singlet oxygen production, that is expressed by the photoinactivation of eukaryotic and prokaryotic cells.

The photosensitizers described by this invention are able to produce singlet oxygen by using various light sources and wavelengths. In particular they can be activated by visible red light radiation when the treatment of deep seated tumours on infections is required as well as by blue visible radiation or white light radiations when is preferable to treat by means of the photodynamic process more superficial lesions such as in the treatment of psoriasis, actinic keratoses, basal cell carcinomas and other cancerous and pre-cancerous lesions of the skin and mucosas. Of particularly interest is the possibility to modulate the activity of these products by acting on the radiation wavelength used for the activation. In fact it is well known that porphyrins are able to absorb light in the red region and in the blue region of the visible spectrum to a different extent. The combination of the light source devised to these purposes and the differential absorption by the porphyrins, allows a unique possibility in order to precisely define the activity of these compounds while used as photosensitizers in the photodynamic treatment of the above mentioned pathologies.

The present compounds are therefore suitable for the photodynamic treatment of pathologies characterised by cellular hyperproliferation and for the photodynamic treatment of infections caused by pathogenic micro-organisms, however can be also used as in vivo diagnostic agents due to the fluorescence released after excitation at various wavelength in the visible region of the light spectrum. Finally these derivatives can be used as sterilizing agents in the in vivo treatment such as the treatment of wounds as well as in vitro treatments such as the blood or blood derivatives sterilisation.

Subject of the present invention are therefore the porphyrins of general formula (I)

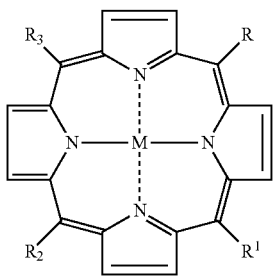

wherein
R is the following group of formula (II)

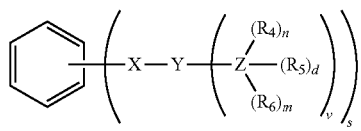

wherein
X is selected from the group consisting of O, S, $CH_2$, COO, $CH_2CO$, $O(CH_2)_2O$, $O(CH_2)_3O$ and N;
Z is selected from between N and $CH_2N$;
Y is selected from aliphatic groups, linear or branched, saturated or unsaturated, having from 1 to 10 carbon atoms, and phenyl, possibly substituted, or Y forms with Z a saturated or unsaturated heterocycle, possibly substituted, comprising up to two heteroatoms selected from the group consisting of N, O and S;
$R_4$ and $R_5$, equal or different from each other, are selected from H and alkyl groups having from 1 to 3 carbon atoms, or they form with the Z group a saturated or unsaturated heterocycle, possibly substituted, comprising up to two heteroatoms selected from the group consisting of N, O and S;
$R_6$ is selected from H and aliphatic groups, linear or branched, saturated or unsaturated, having from 1 to 5 carbon atoms, possibly substituted with alkylamine or alkylammonium groups having alkyl chains comprising from 1 to 5 carbon atoms, or forming a saturated heterocycle comprising up to two heteroatoms selected from between O and N;
d, m, and n, equal of different from each other, are selected from 0 and 1;
v and s, equal or different from each other, are integers comprised between 1 and 3;
$R_1$ is selected from H and a group of formula (III)

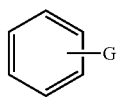

wherein
G is selected from H and P—$(CH_2)_I$—$(W)_f$-J, wherein
P is selected from the group consisting of O, $CH_2$, $CO_2$, NHCONH and CONH;
I is an integer comprised between 0 and 5;
W is selected from the group consisting of 0, $CO_2$, CONH and NHCONH;
f is selected from between 0 and 1;
J is H or an alkyl group $(CH_2)_q$—$CH_3$, wherein q is an integer comprised between 0 and 20;
$R_2$ and $R_3$, equal or different from each other, are selected from between R and $R_1$, wherein R and $R_1$ are defined as above,
M is chosen from 2H and a metal selected from the group consisting of Zn, Mg, Pt, Pd, $Si(OR_7)_2$, $Ge(OR_7)_2$ and $AlOR_7$, wherein $R_7$ is chosen from between H and C1-C15 alkyl,
and pharmaceutically acceptable salts thereof,
with the exception of the following compounds:
a) compound of formula (I) wherein M is 2H, $R_1=R_3=H$, $R=R_2$ is a group of formula (II) in which s is 1, X is O, Y is $(CH_2)_3$, v is 1, Z is N, n=d=1, m is 0, and $R_4=R_5=H$; and
b) compound of formula (I) wherein M is 2H, $R_1=R_3=H$, $R=R_2$ is a group of formula (II) in which s is 1, X is O, Y is $(CH_2)_3$, v is 1, Z is N, n=d=1, m is 0, $R_4$ and $R_5$ form with Z a phthalimido group.

Further subject of the present invention are the processes for the preparation of the above said compounds of formula (I), the novel intermediates in these processes and the conjugates in which the compounds of formula (I) are site specifically conjugated with bio-organic carriers, such as aminoacids, polypeptides, proteins and polysaccharides.

The present compounds of formula (I), as well as the corresponding conjugates, are useful for the treatment of microbial infections (bacterial, fungal and viral), in the photodynamic treatment of tumour, pre-cancerous pathologies, and other hyperproliferative diseases.

The present compounds (I) and the corresponding conjugates are useful as well, as diagnostic agents for the identification of pathologically affected areas and for photodynamic sterilization of blood and blood derivatives.

Features and advantages of the present compounds of formula (I) will be illustrated in details in the following description.

DETAILED DESCRIPTION OF THE INVENTION

By "saturated or unsaturated heterocycle possibly substituted" according to the invention, an heterocycle is preferably meant, which is selected from the group consisting of morpholine, piperidine, pyridine, pyrimidine, piperazine, pyrrolidine, pyrroline, imidazole, and julolidine (2,3,6,7-tetrahydro-1H,5H pirido[3,2,1-lj]quinoline).

According to a particular embodiment of the invention, the present porphyrins of formula (I) have two or three groups with amino or ammonium substituents in two or three of the four meso-positions, and H or groups with non polar substituents on the other meso-positions.

Preferred compounds according to the invention are those wherein the group R comprises substituents bearing tertiary or quaternary nitrogen; more preferred are the present compounds of formula (I) wherein the group is selected from the group consisting of:

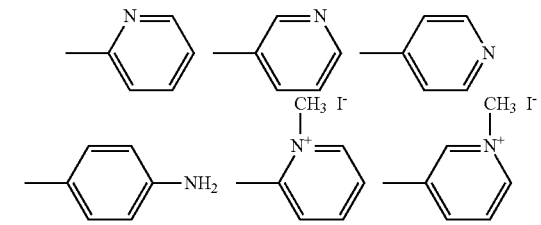

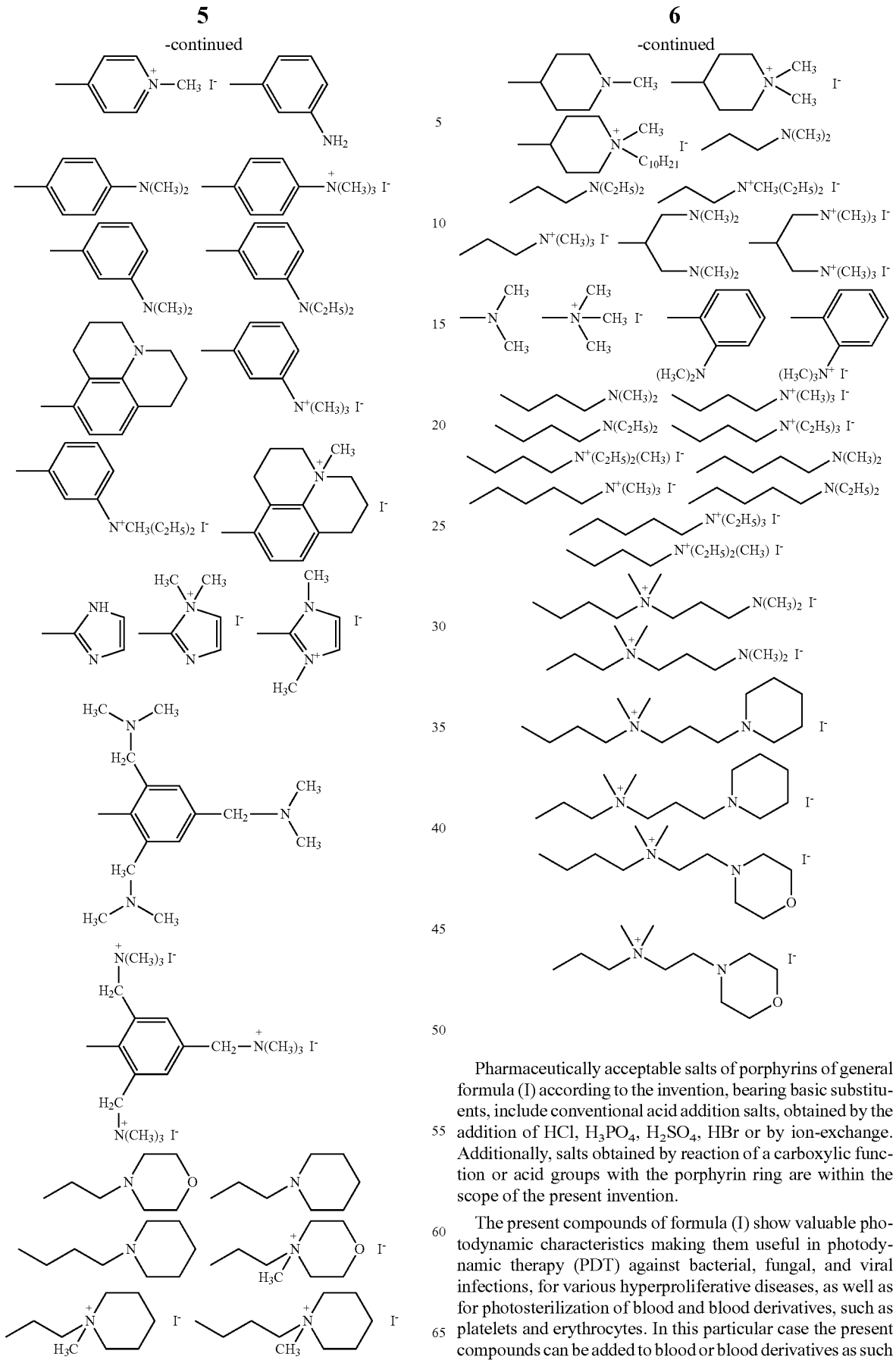

Pharmaceutically acceptable salts of porphyrins of general formula (I) according to the invention, bearing basic substituents, include conventional acid addition salts, obtained by the addition of HCl, $H_3PO_4$, $H_2SO_4$, HBr or by ion-exchange. Additionally, salts obtained by reaction of a carboxylic function or acid groups with the porphyrin ring are within the scope of the present invention.

The present compounds of formula (I) show valuable photodynamic characteristics making them useful in photodynamic therapy (PDT) against bacterial, fungal, and viral infections, for various hyperproliferative diseases, as well as for photosterilization of blood and blood derivatives, such as platelets and erythrocytes. In this particular case the present compounds can be added to blood or blood derivatives as such or bound to suitable matrix, according to the known techniques, and thereafter irradiated. Moreover they can be used as diagnostic agents for the identification of pathologically affected areas.

The present products possess a high molar absorption coefficient, which represents an important requirement for an effective therapeutic response. They may be activated by tissue penetrating radiation having a wavelength around 650 nm, and hence they are suitable for the use in PDT against diseases, both dermatological and internal, but they also can be activated by using less tissue penetrating light for the photodynamic treatment of very superficial lesion, especially when a little damage of the skin should be accomplished or, for instance, when a fluorescence emission from the tissue is preferred such as in the photodiagnostic procedures of the above mentioned pathologies.

The products formed by photobleaching of the present compounds are non toxic. This finding reinforces their usefulness as therapeutic since, after having exploited their action, the compounds are inactivated by the light and then are no more potentially toxic in vivo.

The present compounds are active in the singlet oxygen production or allow the production of reactive species of oxygen under conditions of poor oxygenation. Such requirement is particularly important because it allows to treat specifically anaerobic micro-organisms or tumour cells, well-known characterised by an environment poor of oxygen.

In particular, the present compounds possess very high efficiency for micro-organisms such as yeasts, fungi and mycoplasma, Gram-positive and Gram-negative bacteria, and show a great ability in specifically localizing on micro-organisms compared to the mammalian host cells.

The present invention comprises also the above described formula (I) compounds site-specifically conjugated with a bio-organic carrier able to direct to a definite target.

According to the invention the carrier is usually chosen among molecules having well-known specific binding capacities, for example aminoacids (preferably basic aminoacids), polypeptides (preferably consisting of basic aminoacids), proteins and polysaccharides normally used for targeting purposes.

The binding porphyrin/carrier may occur for example between the corresponding amino or carboxyl groups, or may occur involving other specific functional groups on the porphyrin moiety or on the carrier molecule.

Functional groups such as thiol, maleimide derivatives, a-bromo esters and amides, diazonium salts and azido derivatives can be introduced according to known procedures in order to pre-functionalize both the porphyrin or the carrier depending upon the selected carrier itself and its stability.

The compounds of the present invention can be prepared according to processes known in organic chemistry starting from suitable reagents. For example, when compounds of formula (I) in which $R=R_2=R_3$ are desired, they can be prepared according to a process selected from the group consisting of:

process comprising pre-functionalization of suitable reagents with amino groups, followed by statistical synthesis of the porphyrin ring, possible modification of the amino groups in ammonium groups, and possible complexation with the metal cation if the metal complex is required;

process comprising statistical synthesis with formation of the porphyrin ring followed by functionalization of the porphyrin with the present amino or ammonium groups, and possible complexation with the metal cation; and process comprising synthesis of the porphyrin ring through suitable dipyrromethane derivatives followed by functionalisation of the porphyrin with the present amino or ammonium groups, and possible complexation with the metal cation.

When compounds of formula (I) are desired in which $R=R_2$ and $R_1=R_3$, they can be prepared for example according to a process comprising the synthesis of the porphyrin ring through dipyrromethane followed by functionalisation of the porphyrin with aliphatic or aromatic amino or ammonium groups, and possible complexation with the metal cation if the metal complex is required.

Some examples of the above said processes are illustrated in the following schemes.

SCHEME 1: Synthesis of compounds of formula (I) in which $R = R_2 = R_3$
SCHEME 1A: pre-functionalization of suitable reagents (selected so to form the porphyrin ring) with amino groups, followed by statistical synthesis of the porphyrin ring, and possible modification of the amino groups in ammonium groups

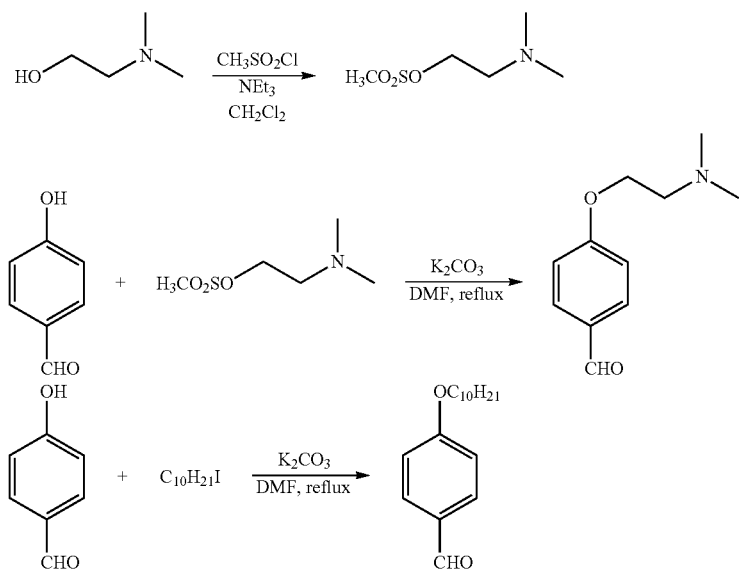

-continued
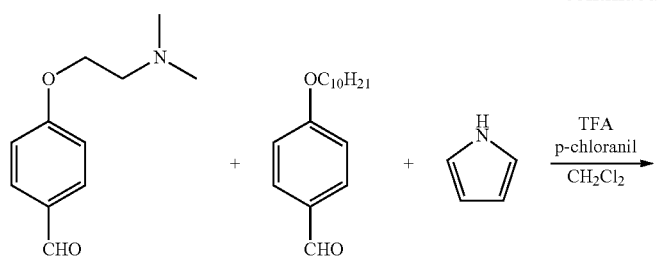
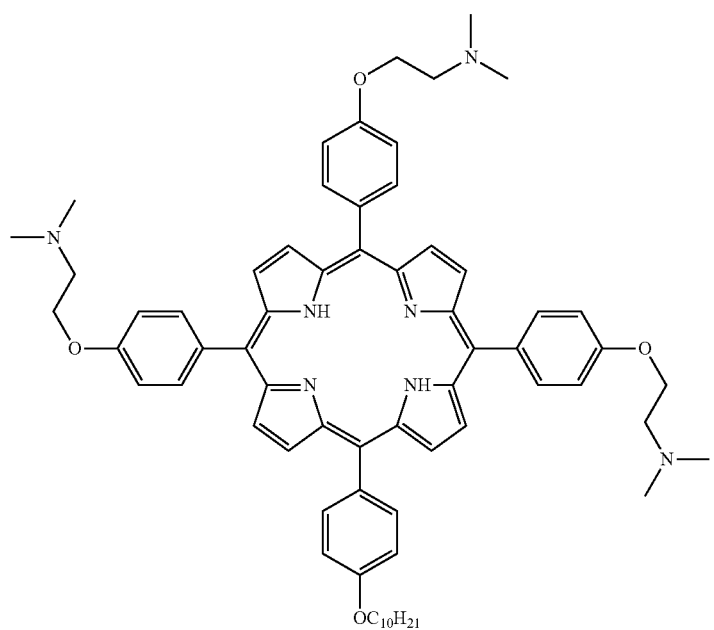
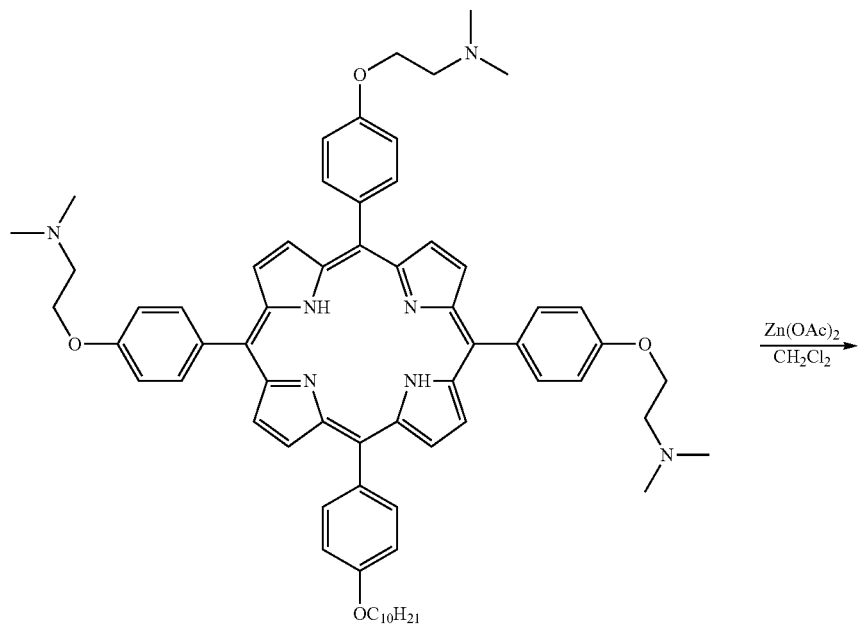

-continued
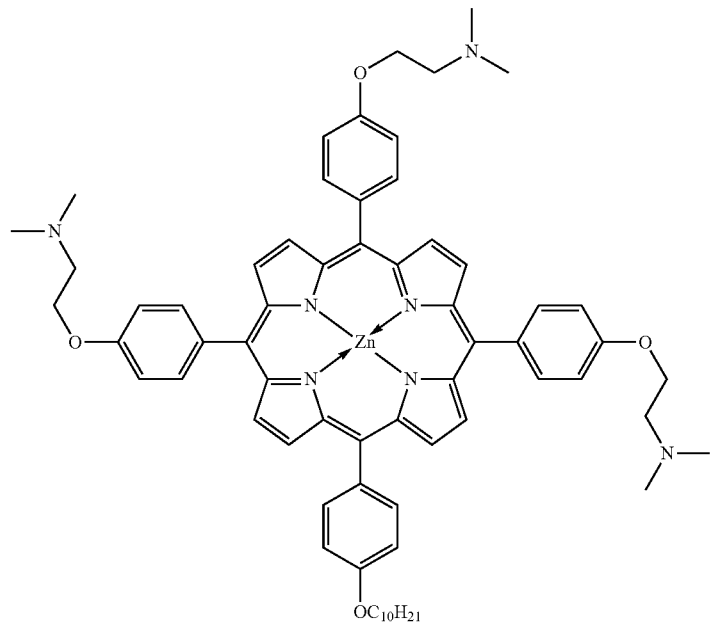
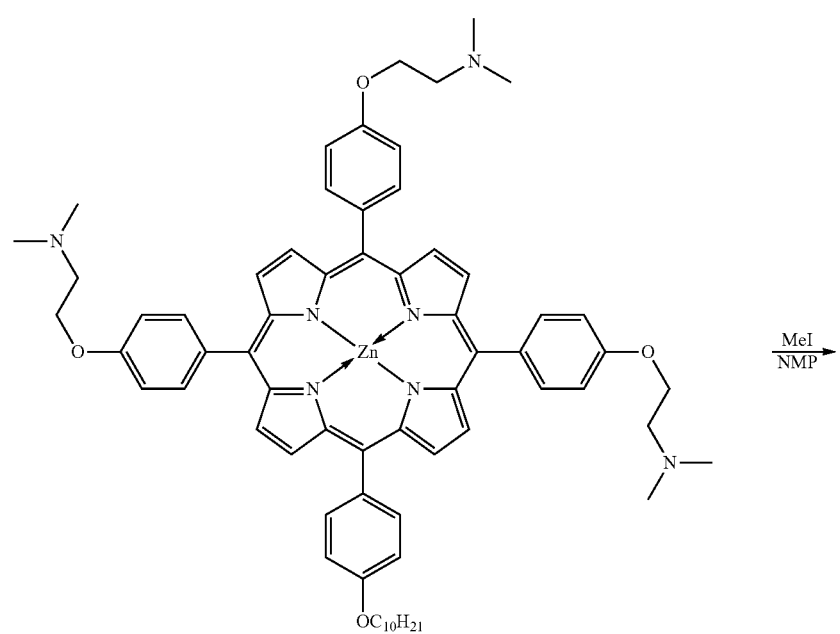

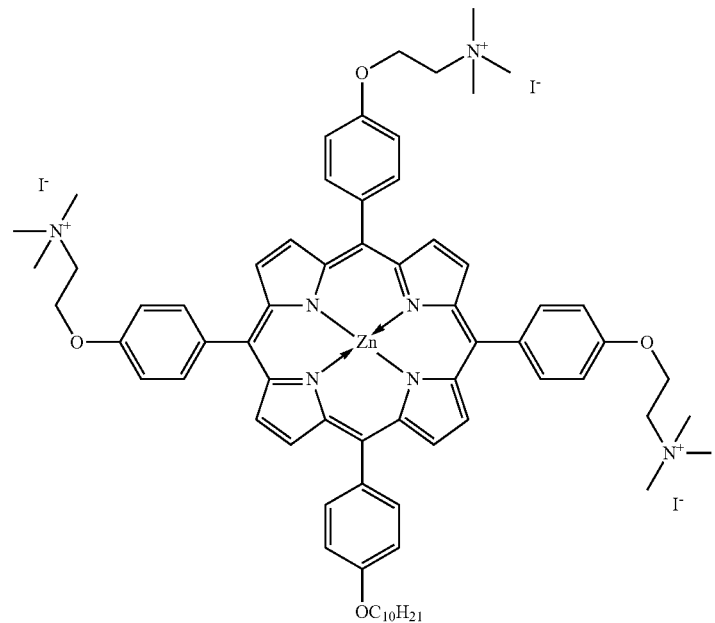
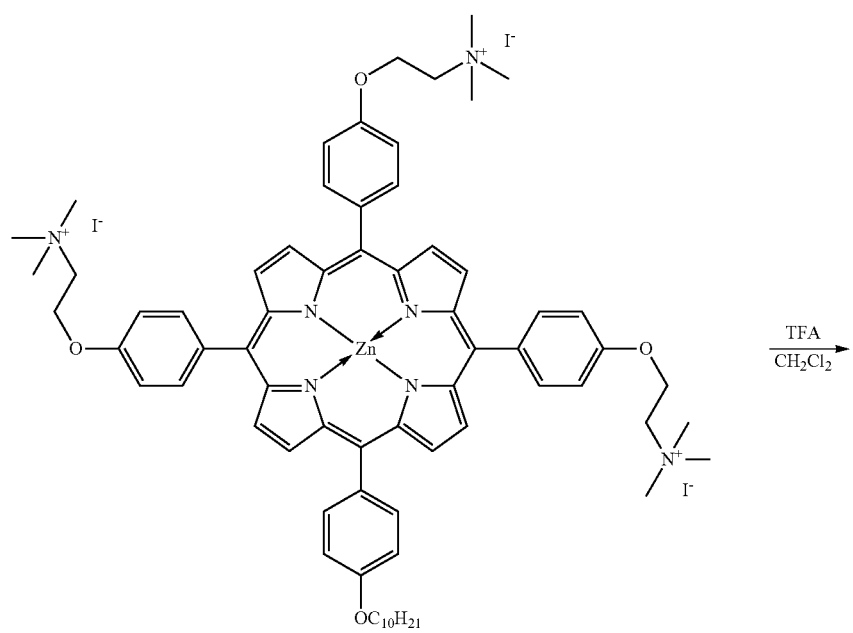

-continued
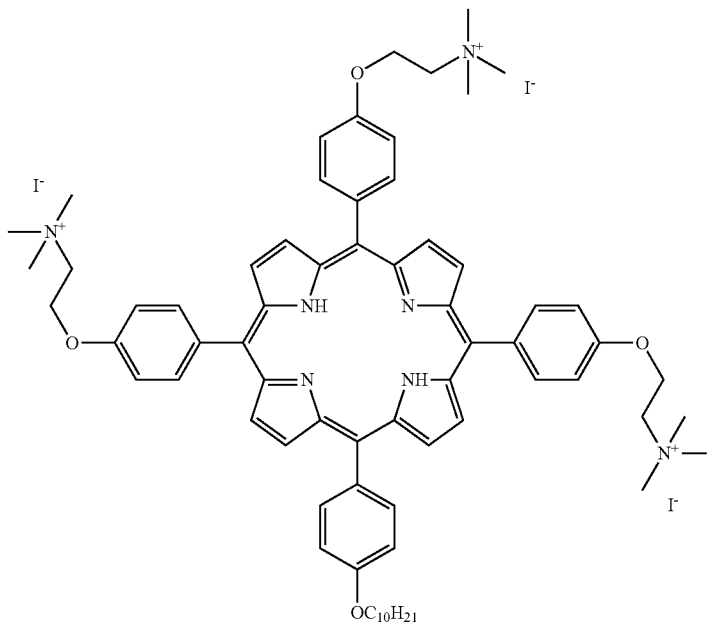
SCHEME 1B: statistical synthesis with formation of the porphyrin ring followed by functionalization of the porphyrin with the present amino or ammonium groups
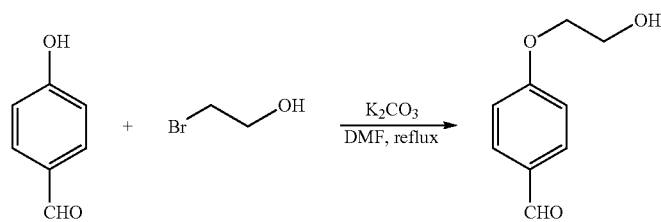
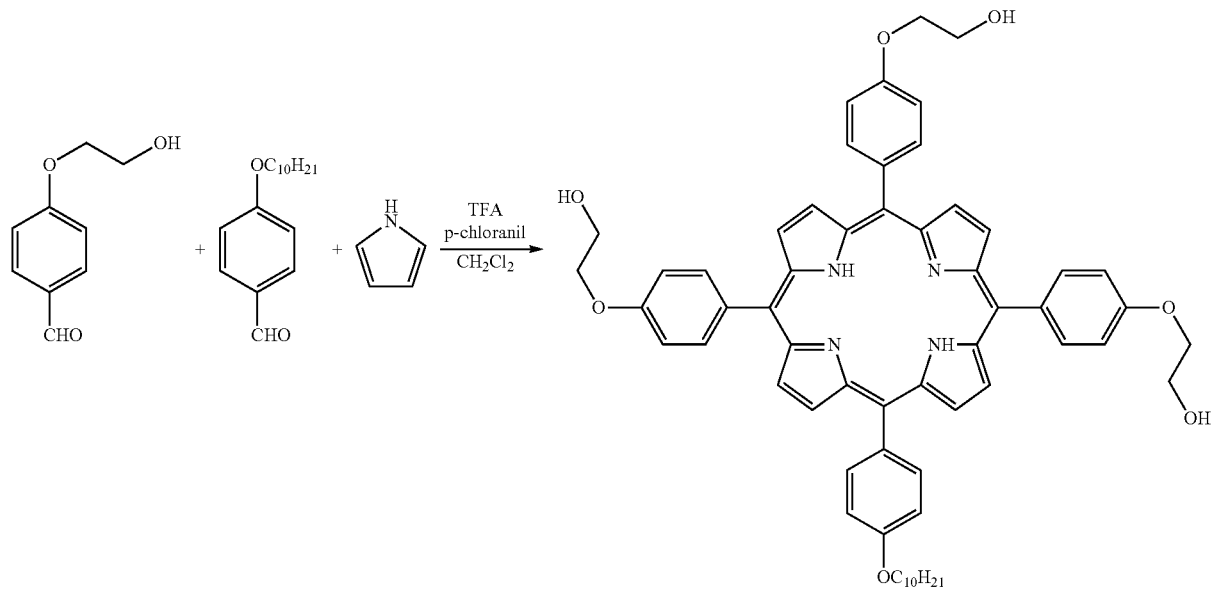

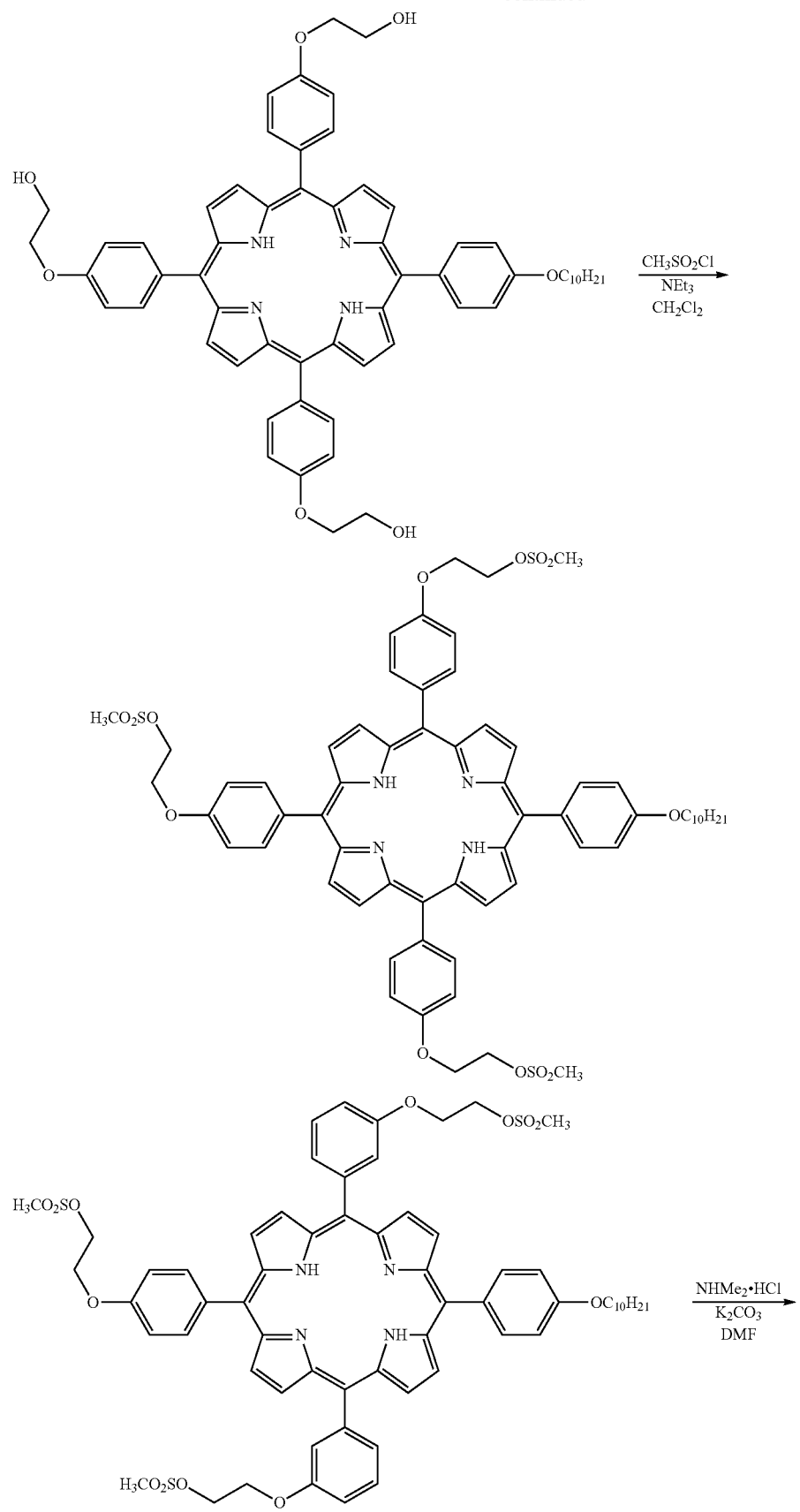

-continued
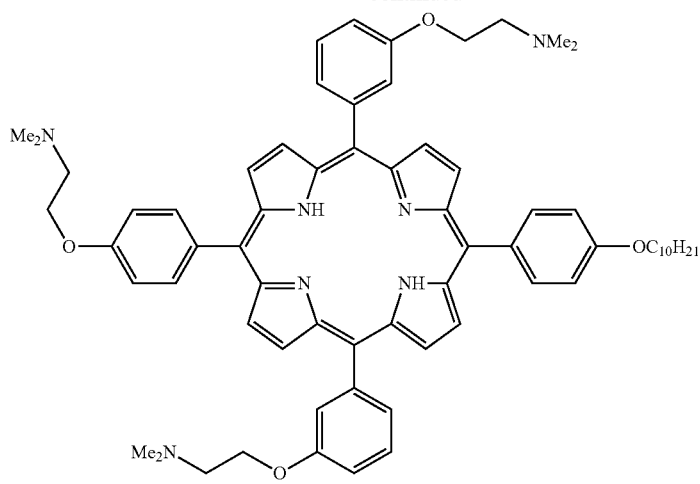
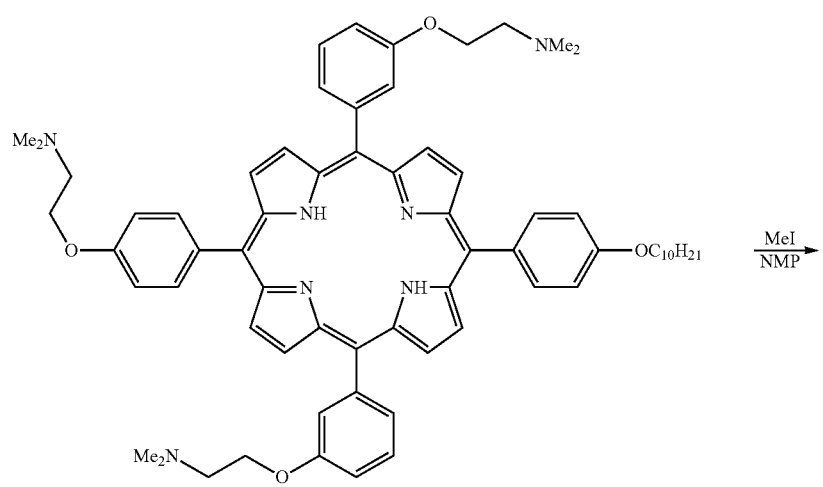
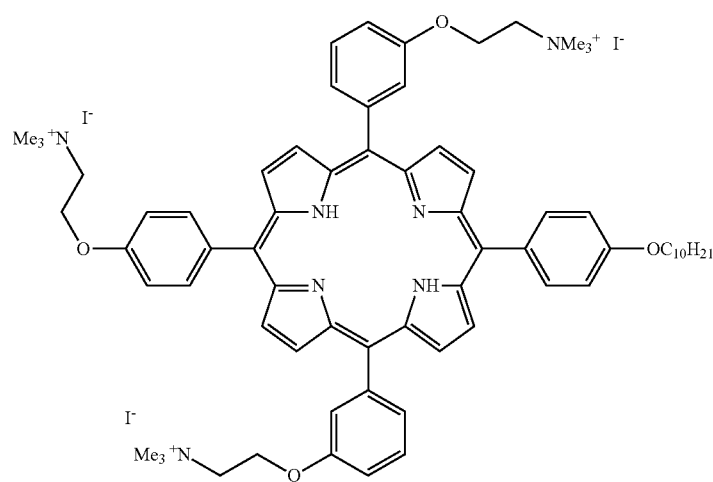

SCHEME 1C: synthesis of the porphyrin ring through suitable dipyrromethane derivatives followed by functionalisation of the porphyrin with the present amino or ammonium groups

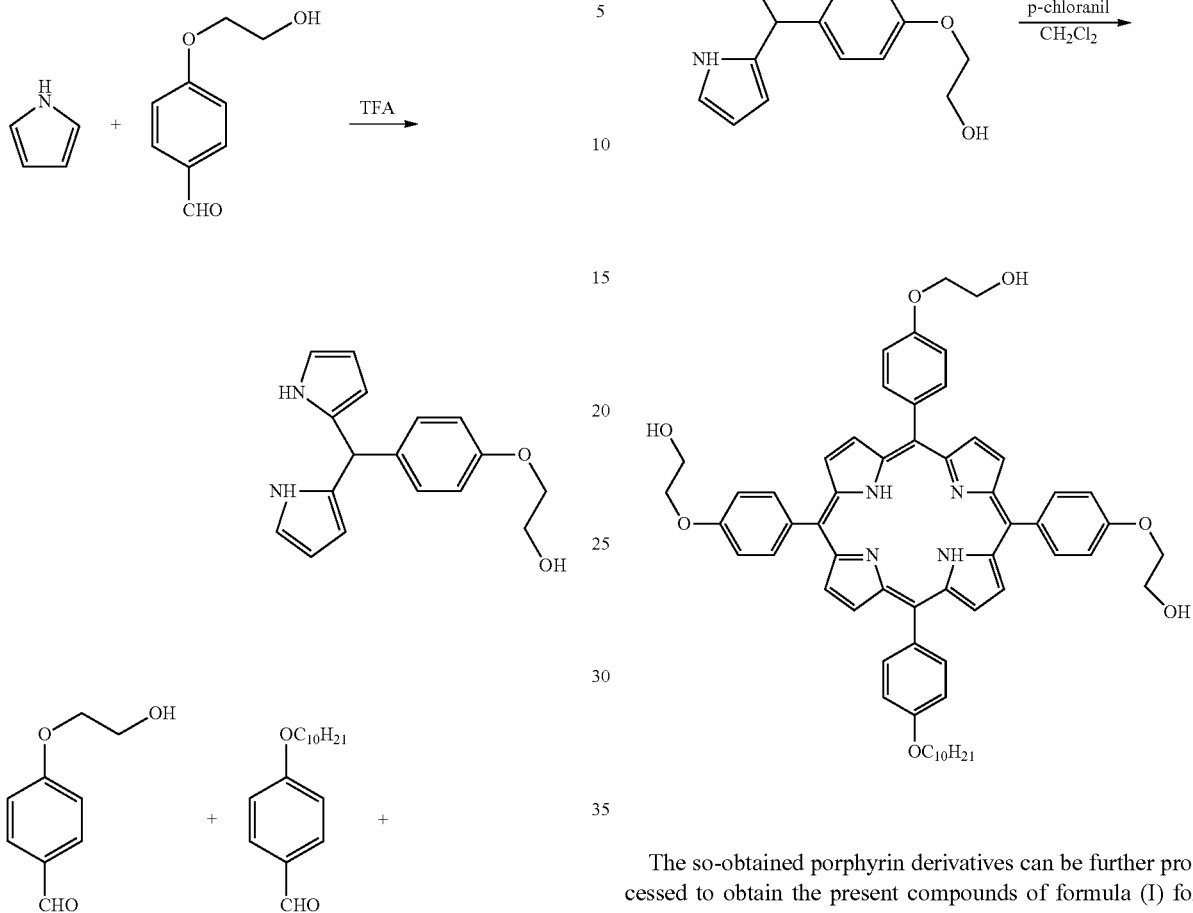

The so-obtained porphyrin derivatives can be further processed to obtain the present compounds of formula (I) for example according to the last three steps in the above Scheme 1B.

SCHEME 2: Synthesis of compounds in which R = $R_2$ and $R_1$ = $R_3$
SCHEME 2A: synthesis of the porphyrin ring through dipyrromethane followed by functionalisation of the porphyrin with aliphatic amino or ammonium groups

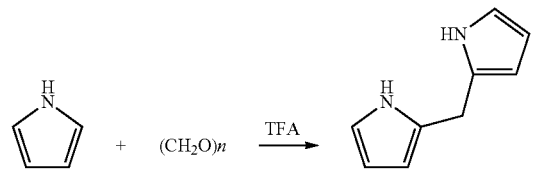

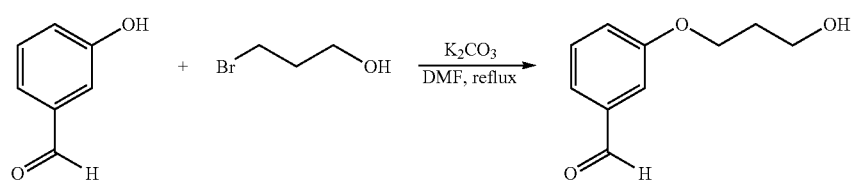

23
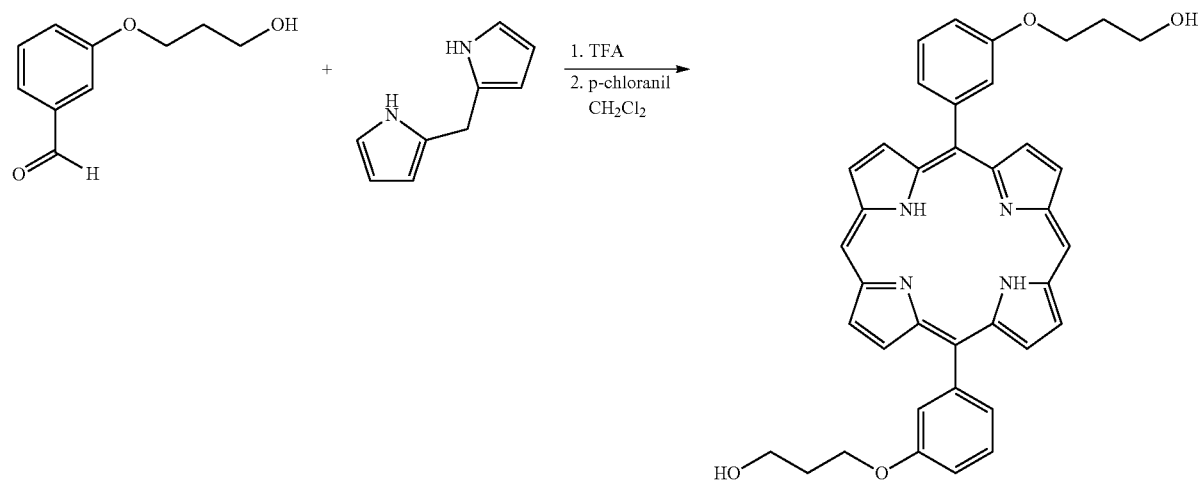
24
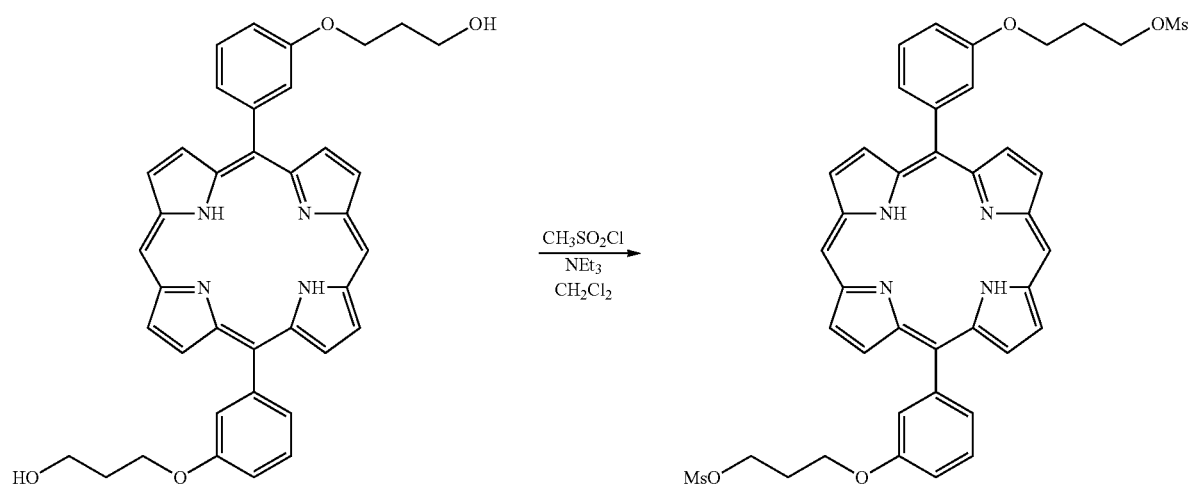
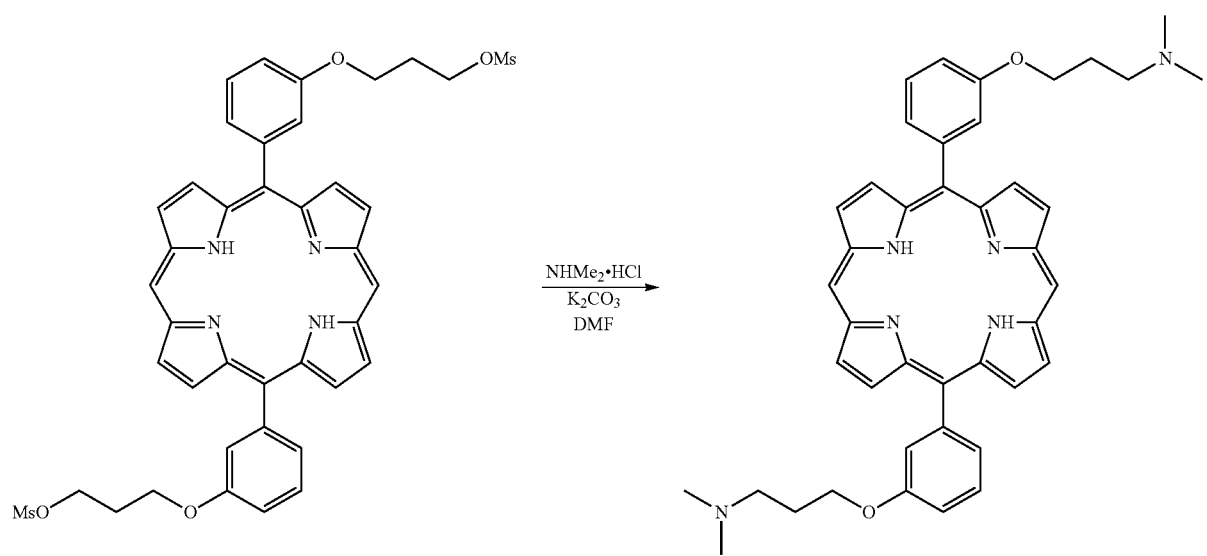

25 26
-continued
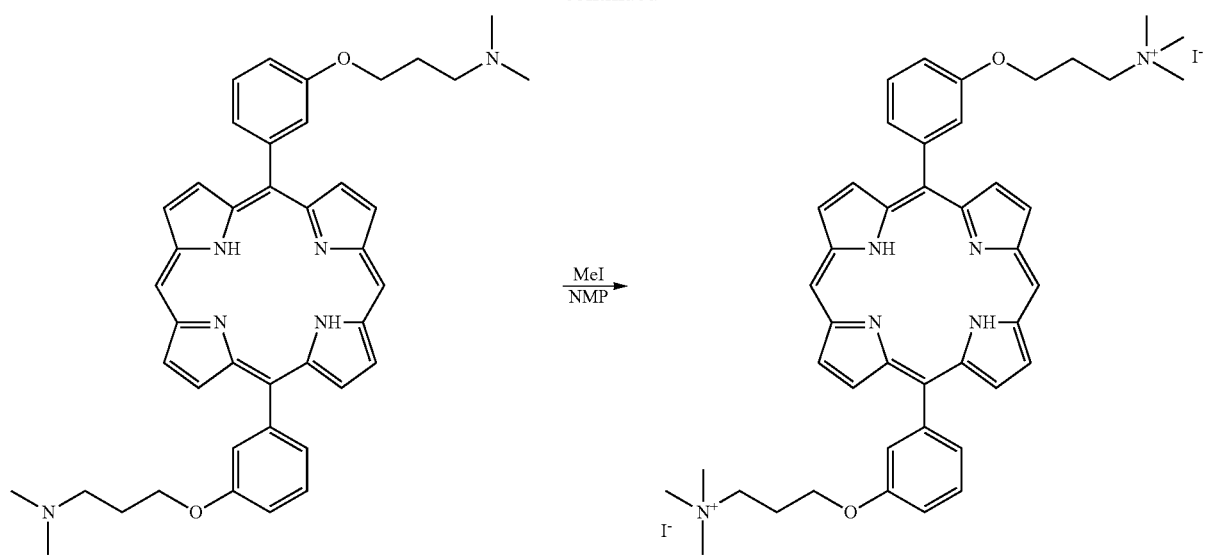
SCHEME 2B: preparation of Zn(II)-porphyrinates bearing aliphatic amino/ammonium groups starting from the corresponding porphyrins bearing aliphatic hydroxy groups
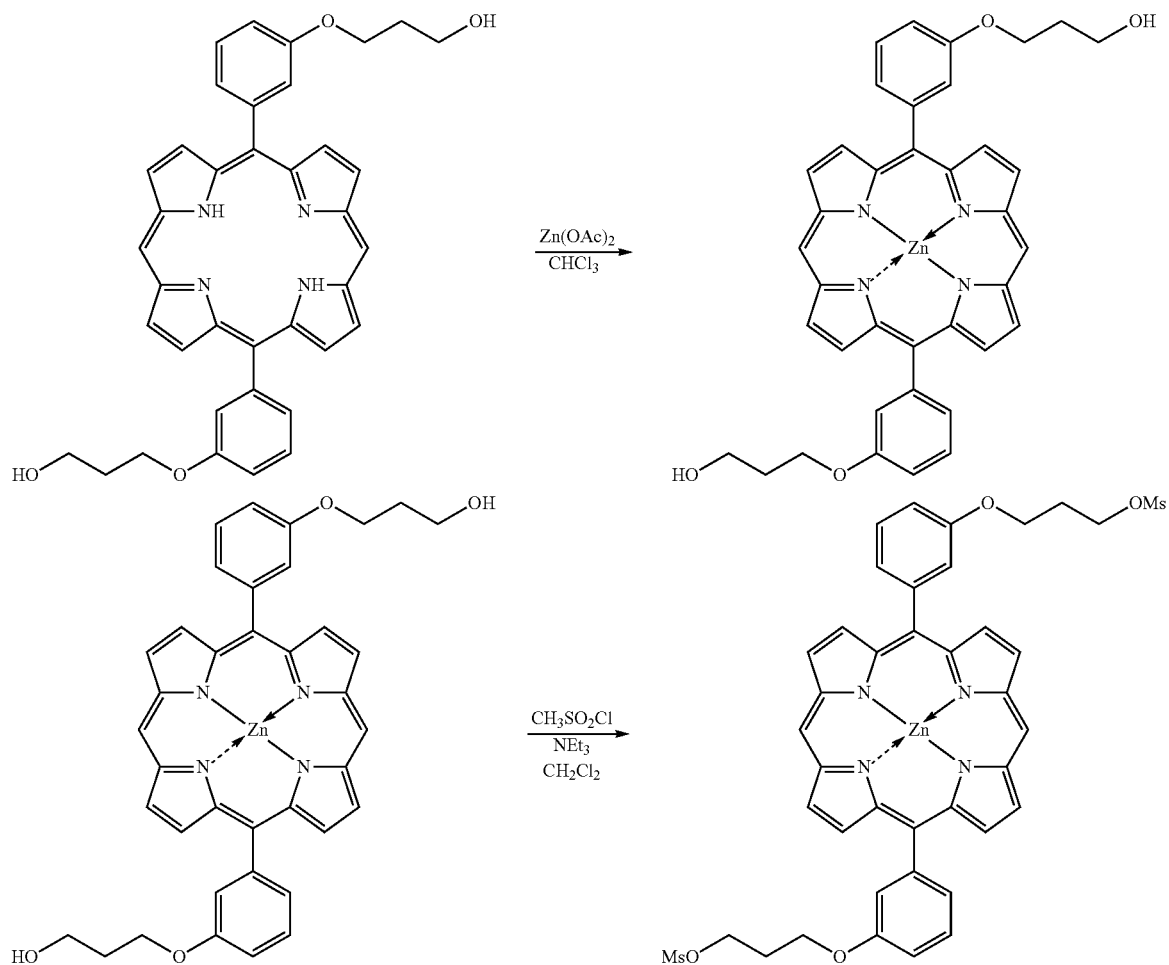

27  28
-continued
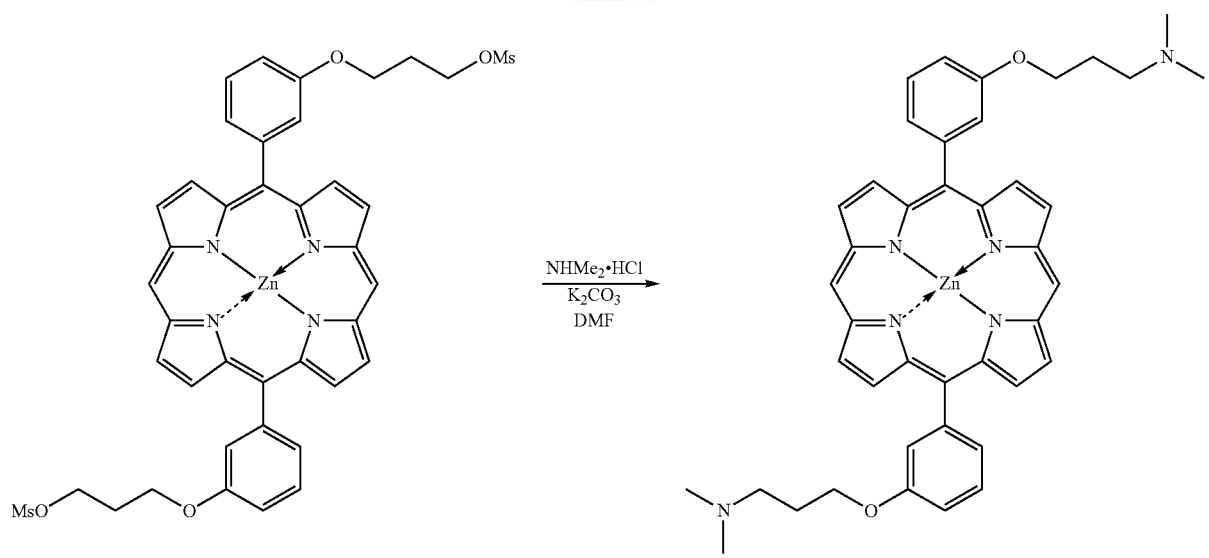
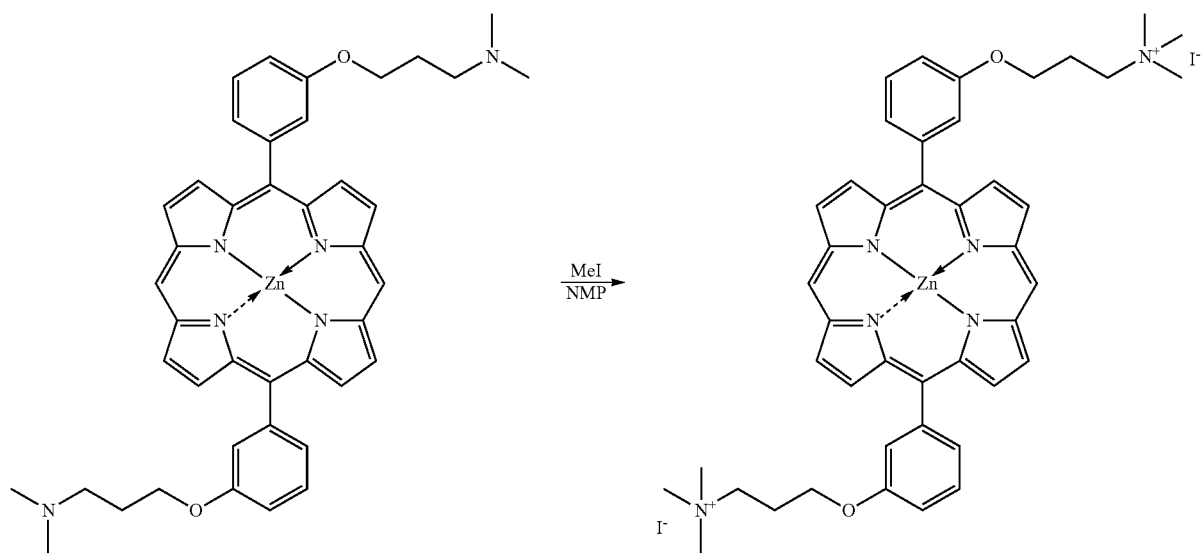
SCHEME 2C: preparation of porphyrins bearing aromatic amino/ammonium groups
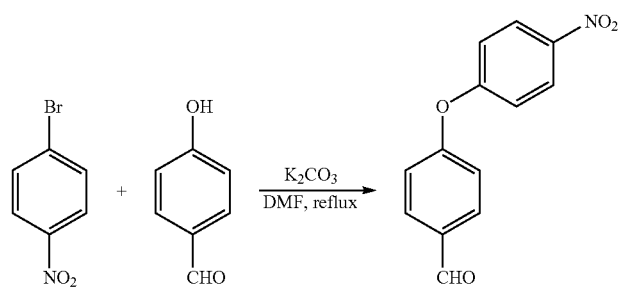

-continued
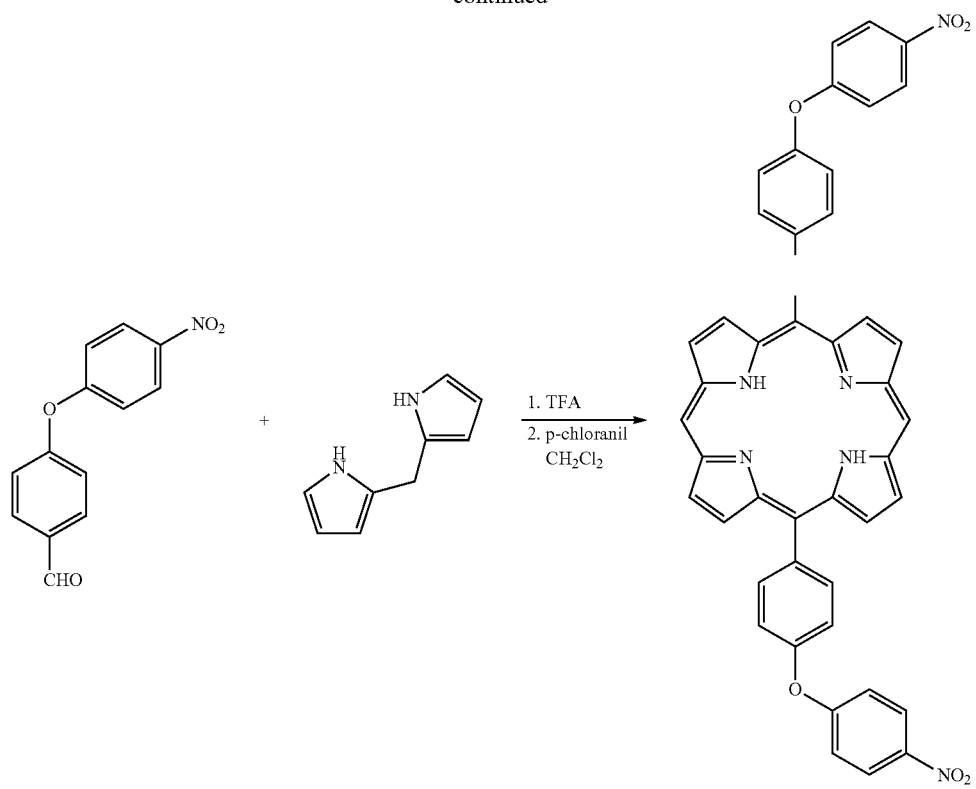
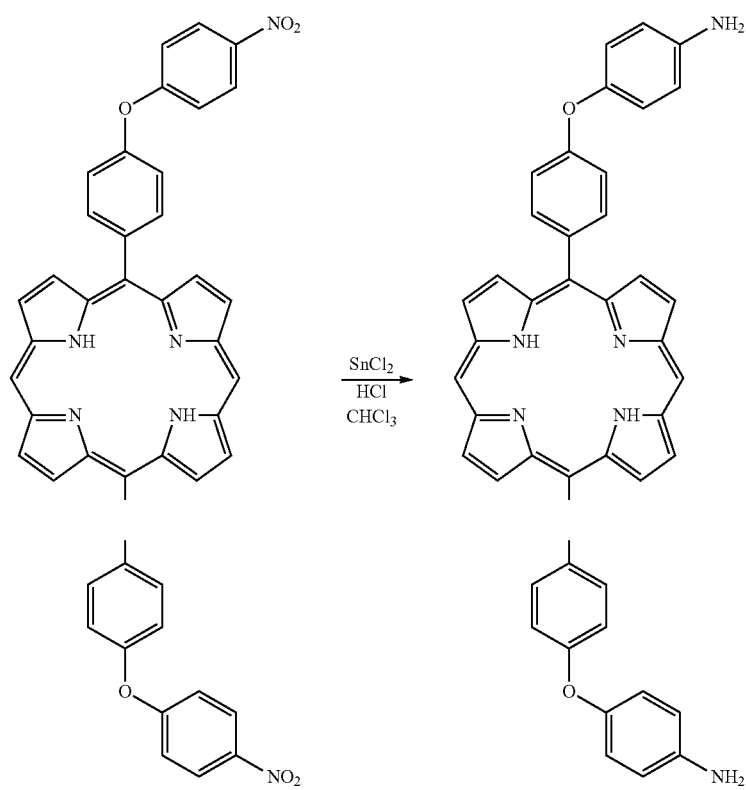

-continued

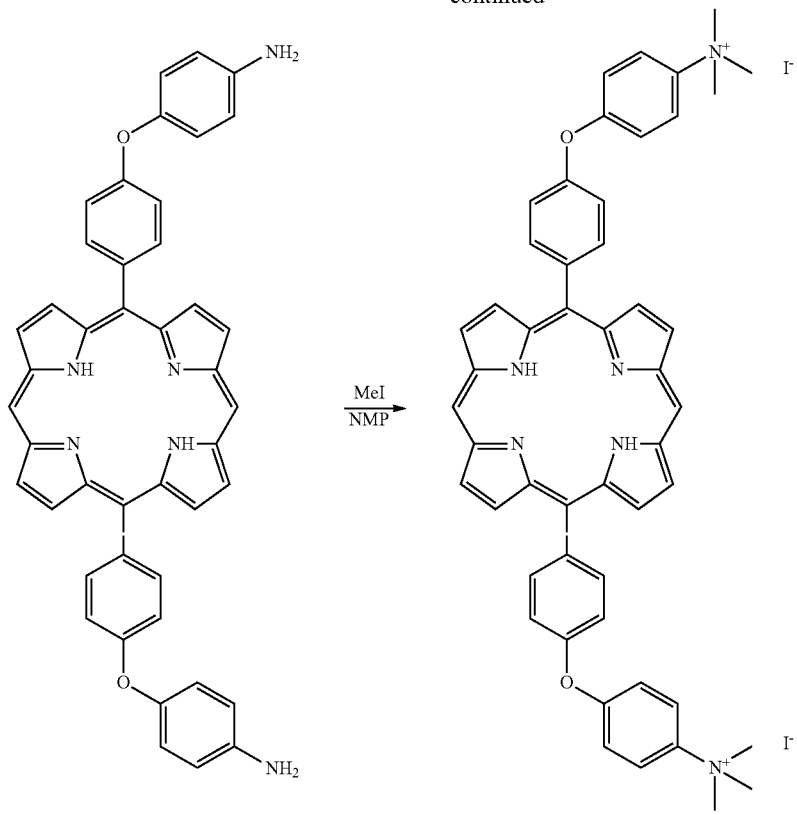

The present porphyrins can be converted in the corresponding metal complexes by treatment with the suitable metal cation according to well-known procedures in organic chemistry. The introduction of the metal cation into the porphyrin ring may be achieved before or after the functionalisation of the porphyrin ring with the present amino or ammonium groups.

All the quaternary ammonium porphyrin iodides derivatives prepared can be easily converted in the corresponding chlorides or other more acceptable salts for biological purposes.

The compounds of the present invention have been prepared according to the procedure described above, identified and characterised by spectroscopic ($^1$H-NMR, $^{13}$C-NMR), spectrophotometric (UV-Vis), and spectrometric (EI, ESI or DCI-MS) analytical techniques.

The following examples are given to provide a non limiting illustration of the invention.

EXAMPLE 1

Synthesis of 5,10,15-tris-[4-(2-N,N,N-trimethylammoniumethoxy)phenyl]-20-[4-decyloxy)phenyl]porphyrin triiodide by statistical synthesis with pre-functionalization Step a) Synthesis of N,N-dimethyl-2-methylsulphonylethylamine To a solution of N,N-dimethylethanolamine (890 mg, 10 mmol) and triethylamine (1520 mg, 15 mmol) in anhydrous $CH_2Cl_2$, kept under nitrogen atmosphere, at 0° C., methansulphonyl chloride (1220 mg, 11 mmol) was added. The mixture was kept under stirring and at 0° C. for 1 hour, and then concentrated by evaporation. The residue was dissolved in $CH_2Cl_2$, washed with $Na_2CO_3$ saturated solution and with deionized water. The organic phase was dried under $Na_2SO_4$ and the solvent removed by evaporation. The product was used as obtained, without purification, for the following step b) (1330 mg, yield 80%).

$^1$H-NMR: (300 MHz, DMSO-d$^6$) 3.51 (2H, t, J=5.8 Hz), 3.03 (6H, s), 3.00 (2H, t, J=5.8 Hz), 2.71 (6H, s)

EI-MS: 167.23 Th $[C_5H_{13}NO_3S]^+$

Step b) Synthesis of 4-(N,N-dimethylaminoethoxy)benzaldehyde

To a solution of 4-hydroxybenzaldehyde (500 mg, 4 mmol) and $K_2CO_3$ (662 mg, 4.8 mmol) in anhydrous DMF, N,N-dimethyl-2-metilsulphonilethylamine (775 mg, 4.4 mmol) was added. The reaction mixture was heated to reflux, under magnetic stirring, for 4 hours, then poured in water to obtain a suspension from which the solid was isolated by filtration. The crude product was purified by chromatography on silica gel (ethyl acetate), to give 379 mg of pure product of the title (yield 49%).

$^1$H-NMR: (300 MHz, DMSO-d$^6$): 9.86 (1H, s), 8.78 (2H, d, J=8.8 Hz), 6.98 (2H, d, J=8.8 Hz), 3.28 (2H, t, 5.5 Hz), 2.97 (2H, t, J=5.5 Hz), 2.71 (6H, s)

EI-MS: 193.25 Th $[C_{11}H_{15}NO_2]^+$

Step c) Synthesis of 4-decyloxybenzaldehyde

To a solution of 4-hydroxybenzaldehyde (732 mg, 6 mmol) in anhydrous DMF (13 ml), under nitrogen atmosphere, $K_2CO_3$ (1658 mg, 12 mmol), and, after 10 minutes, iododecane (1785 mg, 7.2 mmol) were added. The mixture was heated to reflux for 3 hours, then water was added and the product was extracted with $CH_2Cl_2$. The organic layers were washed with water and with NaCl saturated solution, dried with $Na_2SO_4$. After evaporation of the solvent, the crude product was purified by chromatography on silica gel (Petroleum ether/Ethyl acetate 11/1) and 1530 mg (yield 97%) of the pure product of the title were obtained.

$^1$H NMR (300 MHz, DMSO-$d^6$): 9.84 (1H, s), 7.82 (2H, d, J=9 Hz), 7.09 (2H, d, J=9 Hz), 4.06 (2H, t, J=6.6 Hz), 1.71 (2H, tt, J=6.6 Hz, 6.5 Hz), 1.30 (14H, m), 0.83 (3H, t, 6.5 Hz).

$^{13}$C NMR (75 MHz, DMSO-$d^6$): 191.7, 164.2, 132.2, 130.0, 115.3, 68.4, 31.7, 29.4, 29.4, 29.2, 29.1, 28.9, 25.8, 22.5, 14.3.

EI-MS: 262.3 Th $[C_{17}H_{26}O_2]^+$

Step d) Synthesis of 5,10,15-tris-[4-(2-N,N-dimethylaminoethoxy)phenyl]-[20-(4-decyloxy)phenyl]porphyrin To a solution of 4-decyloxybenzaldehyde coming from step c) (505 mg, 2 mmol), 4-(N,N-dimethylaminoethoxy) benzaldehyde prepared as described in step b) (1160 mg, 6 mmol) and pyrrole (537 mg, 8 mmol) in anhydrous $CH_2Cl_2$, trifluoroacetic acid (570 mg, 6.7 mmol) was added and the mixture was kept under magnetic stirring, at room temperature, under nitrogen atmosphere, for 20 hours. Then p-chloranil (1650 mg, 6.7 mmol) was added and the final mixture stirred for additional 4 hours. Work-up: washing with $Na_2CO_3$ saturated solution, drying on $Na_2SO_4$, and removing solvent by evaporation. The crude product was finally purified by reverse phase chromatography on C18 silica gel (water/acetonitrile 3/1), to give 245 mg of the title product (yield 12%).

$^1$H NMR (300 MHz, CDCl$_3$): 8.85 (8H, m), 8.11 (8H, m), 7.29 (8H, m), 4.40 (6H, t, J=5.6 Hz), 4.25 (2H, t, J=6.3 Hz), 2.99 (6H, t, J=5.6 Hz), 2.53 (18H, s), 1.97 (2H, tt, J=7.2 Hz), 1.65-1.32 (14H, m), 0.91 (3H, t, J=6.6 Hz); −2.77 (2H, s).

$^{13}$C NMR (75 MHz, CDCl$_3$, selected data): 163.4, 163.0, 161.8, 135.6, 131.1, 118.0, 112.7, 77.2, 68.3, 66.8, 58.1, 49.1, 44.4, 37.7, 31.9, 29.6, 29.4, 29.3, 26.2, 22.6, 14.0.

ESI-MS: m/z 1032.5 Th $[C_{66}H_{78}N_7O_4]^+$.

Step e) Synthesis of 5,10,15-tris-[4-(2-N,N-dimethylaminoethoxy)phenyl]-20-[(4-decyloxy)phenyl]porphyrinate zinc (II)

To a solution of 5,10,15-tris-4-(2-N,N-dimethylaminoethoxy)phenyl]-20-[(4-decyloxy)phenyl]porphyrin coming from step d) (40 mg, 0.04 mmol) in CHCl$_3$, ZnOAc$_2$ (3.7 mg, 0.02 mmol) was added. The reaction mixture was kept under magnetic stirring, at room temperature, for 30 minutes, then filtered in vacuum and the liquid phase concentrated by evaporation to give 34.7 mg of the desired product of the title (yield 80%).

$^1$H-NMR: (300 MHz, DMSO-$d^6$): 8.92-8.77 (6H, m), 8.81-8.68 (2H, m), 8.23-8.17 (6H, m), 8.10 (2H, d, J=8.7 Hz), 7.84 (2H, d, J=8.7 Hz) 7.90-7.81 (6H, m), 3.66 (2H, m), 3.40 (2H, t, J=5.8 Hz), 2.95 (2H, t, J=5.5 Hz), 2.68 (6H, s), 2.01-0.80 (9H, m)

ESI-MS: 1094.5 Th $[C_{66}H_{76}N_7O_4Zn]^+$

Step f) Synthesis of 5,10,15-tris-[4-(2-N,N-trimethylammoniumethoxy)phenyl]-20-[(4-decyloxy)phenyl]porphyrinate zinc (II) triiodide To a solution of 5,10,15-tris-[4-(2-N,N-dimethylaminoethoxy)-phenyl]-20-[(4-decyloxy)phenyl]porphyrinate zinc (II) coming from step e) (20 mg, 0.02 mmol) in dry NMP, iodomethane (0.6 mmol) was added. The reaction mixture was kept under magnetic stirring, at room temperature, for 8 hours, and then diethyl ether was added slowly until a precipitate appeared. The suspension was filtered and the solid re-crystallised from CHCl$_3$/diethyl ether to give 22.9 mg of pure product of the title (yield 75%).

$^1$H-NMR: (300 MHz, DMSO-$d^6$): 8.90-8.72 (6H, m), 8.81-8.65 (2H, m), 8.26-8.12 (6H, m), 8.15 (2H, d, J=8.7 Hz), 7.84 (2H, d, J=8.7 Hz) 7.80-7.74 (6H, m), 3.66 (2H, m), 4.30 (2H, t, J=5.6 Hz), 2.95 (2H, t, J=5.5 Hz), 3.43 (6H, s), 2.07-0.75 (9H, bm)

ESI-MS: m/z 379.5 Th $[C_{69}H_{84}N_7O_4Zn]^{3+}$

Step g) Synthesis of 5,10,15-tris-[4-(2-N,N,N-trimethylammoniumethoxy)phenyl]-20-[(4-decyloxy)phenyl]porphyrin triiodide To a solution in CHCl$_3$ of 5,10,15-tris-[4-(2-N,N,N-trimethylammoniumethoxy)phenyl]-20-[(4-decyloxy)phenyl] porphyrinate zinc (II) triiodide coming from step f) (30 mg, 0.02 mmol) TFA was added. The mixture was kept at room temperature for 20 minutes, then filtered through K$_2$CO$_3$, and the solvent remove by evaporation, to give 26.3 mg of product of the title (yield 90%).

$^1$H NMR (300 MHz, CD3OD): 8.86 (8H, m), 8.49 (8H, m), 7.69 (6H, m), 7.57 (2H, m), 4.91 (6H, m), 4.35 (2H, t, J=6 Hz), 4.11 (6H, m), 3.46 (27H, s), 2.00 (2H, m), 1.67 (2H, J=6 Hz), 1.56-1.28 (12H, m), 0.92 (3H, t, J=6.6 Hz).

$^{13}$C NMR (75 MHz, CD$_3$OD, selected data): 149.5, 140.3, 134.7, 130.0, 114.4, 112.7, 98.8, 68.4, 65.5, 62.5, 53.8, 31.9, 29.6, 29.5, 29.4, 29.3, 26.1, 22.5, 13.2.

ESI-MS: m/z 358.8 Th $[C_{69}H_{86}N_7O_4]^{3+}$.

EXAMPLE 2

Synthesis of 5,10,15-tris-[4-(2-N,N,N-trimethylammoniumethoxy)phenyl]-20-[(4-decyloxy)phenyl] porphyrin triiodide by statistical synthesis with functionalization on the porphyrin Step a) Synthesis of 4-(2-hydroxyethoxy)benzaldehyde To a solution of 4-hydroxybenzaldehyde (366 mg, 3 mmol) in anhydrous DMF (7 ml), under nitrogen atmosphere, K$_2$CO$_3$ (829 mg, 6 mmol), and, after 10 minutes, bromoethanol (450 mg, 3.6 mmol) were added. The mixture was heated to reflux for 3 hours, then water was added and the product was extracted with CH$_2$Cl$_2$. The organic layers were washed with water and with NaCl saturated solution, dried with Na$_2$SO$_4$. After evaporation of the solvent, the crude product was purified by chromatography on silica gel (Petroleum ether/Ethyl acetate 2/1); 400 mg (yield 80%) of pure product of the title were obtained.

$^1$H NMR (300 MHz, DMSO-$d^6$): 9.85 (1H, s), 7.84 (2H, d, J=8.7 Hz), 7.12 (2H, d, J=8.7 Hz), 4.87 (1H, t, J=5.1 Hz), 4.10 (2H, dt, J=5.1 Hz, 4.8 Hz), 3.73 (1H, t, J=4.8 Hz).

$^{13}$C NMR (75 MHz, DMSO-$d^6$): 191.7, 164.2, 132.2, 130.0, 115.4, 70.5, 59.8.

Step b) Synthesis of 5,10,15-tris-[4-(2-hydroxyethoxy)phenyl]-20-[(4-decyloxy)phenyl]porphyrin To a solution of 4-decyloxybenzaldehyde (190 mg, 0.72 mmol), 4-(2-hydroxyethoxy)benzaldehyde (360 mg, 2.17 mmol) and pyrrole (241 mg, 3.6 mmol) in dry CH$_2$Cl$_2$, trifluoroacetic acid (228 mg, 2 mmol) was added and the mixture was kept under magnetic stirring, at room temperature, under nitrogen atmosphere, for 4 hours. Then p-chloranil (492 mg, 2 mmol) was added and the final mixture stirred for additional 15 hours, then the organic phase was washed with $Na_2CO_3$ saturated solution, dried on $Na_2SO_4$ and the solvent removed by evaporation. The crude product was purified by chromatography on silica gel (THF/petroleum ether 1/1+1% TEA, to THF+1% TEA), to give 75 mg of the title product (yield 10%).

$^1$H NMR (300 MHz, CDCl$_3$): 8.87 (8H, m), 8.10 (8H, m), 7.27 (8H, m), 4.37 (6H, t, J=4.2 Hz), 4.21 (3H, m), 4.15 (8H, m); 1.96 (2H, tt, J=7.5 Hz), 1.57-1.25 (14H, m), 0.90 (3H, t, J=6.9 Hz); −2.76 (2H, s).

$^{13}$C NMR (75 MHz, CDCl$_3$, selected data): 159.0, 158.4, 135.6, 135.1, 134.3, 131.0, 120.0, 119.6, 112.7, 77.2, 69.4, 68.3, 61.6, 31.9, 29.6, 29.6, 29.5, 29.4, 29.3, 26.2, 22.6, 14.1.

ESI-Ms: m/z 951.2 Th $[C_{60}H_{63}N_4O_7]^+$.

Step c) Synthesis of 5,10,15-tris-[4-(2-methylsulphonylethoxy)phenyl]-20-(4-decyloxy)phenyl]porphyrin To a solution of 5,10,15-tris-[4-(2-hydroxyethoxy)phenyl]-20-(4-decyloxy)phenyl]porphyrin (70 mg, 0.073 mmol) in anhydrous $CH_2Cl_2$, under nitrogen atmosphere, at 0° C., triethylamine (73 mg, 0.73 mmol) and methansulphonyl chloride (42 mg, 0.37 mmol) were added. The mixture was kept under magnetic stirring at room temperature for 3 hours, then washed with $NaHCO_3$ saturated solution and with water. The organic phase was dried with $Na_2SO_4$ and the solvent removed by evaporation. The crude product was purified by chromatography on silica gel ($CH_2Cl_2$/MeOH 50/1), to obtain 65 mg of the title product (yield 65%).

$^1$H NMR (300 MHz, CDCl$_3$): 8.87 (8H, m), 8.12 (8H, m), 7.29 (8H, m), 4.77 (6H, t, J=4.5 Hz), 4.54 (6H, t, J=4.5 Hz), 4.25 (2H, t, J=6 Hz), 3.24 (9H, s), 1.96 (2H, tt, J=8 Hz), 1.61-1.25 (14H, m), 0.91 (3H, t, J=7 Hz); −2.77 (2H, s).

$^{13}$C NMR (75 MHz, CDCl$_3$, selected data): 159.0, 157.8, 140.3, 135.6, 135.6, 134.2, 130.9, 120.2, 119.4, 114.5, 112.8, 77.2, 68.3, 66.2, 66.1, 37.9, 31.9, 29.6, 29.6, 29.5, 29.3, 26.2, 22.6, 14.1.

ESI-Ms: m/z 1185.1 Th $[C_{63}H_{69}N_4O_{13}S_3]^+$.

Step d) Synthesis of 5,10,15-tris-[4-(2-N,N-dimethylaminoethoxy)phenyl]-20-[(4-decyloxy)phenyl]porphyrin To a solution of 5,10,15-tris-[4-(2-methylsulphonylethoxy)phenyl]-20-(4-decyloxy)phenyl]porphyrin (65 mg, 0.055 mmol) in anhydrous DMF (5 ml), under nitrogen atmosphere, $K_2CO_3$ (46 mg, 0.33 mmol), and, after 10 minutes, dimethylamine hydrochloride (27 mg, 0.055 mmol) were added. The mixture was heated at 80° C. for 20 hours, then water was added and the product was extracted with $CH_2Cl_2$. The organic layers were washed with water and with NaCl saturated solution, then dried with $Na_2SO_4$. After evaporation the crude product was purified by chromatography on silica gel (THF to THF/DMF 4/1). After the chromatography, the product was re-crystallized from $CHCl_3$/Petroleum Ether 1/1 and 26 mg (yield 50%) of the title product were obtained.

$^1$H NMR (300 MHz, CDCl$_3$): 8.85 (8H, m), 8.11 (8H, m), 7.29 (8H, m), 4.40 (6H, t, J=5.6 Hz), 4.25 (2H, t, J=6.3 Hz), 2.99 (6H, t, J=5.6 Hz), 2.53 (18H, s), 1.97 (2H, tt, J=7.2 Hz), 1.65-1.32 (14H, m), 0.91 (3H, t, J=6.6 Hz); −2.77 (2H, s).

$^{13}$C NMR (75 MHz, CDCl$_3$, selected data): 163.4, 163.0, 161.8, 135.6, 131.1, 118.0, 112.7, 77.2, 68.3, 66.8, 58.1, 49.1, 44.4, 37.7, 31.9, 29.6, 29.4, 29.3, 26.2, 22.6, 14.0.

UV-VIS (DMF): $\lambda_{max}$ 651, 555, 518, 430, 408, 264, 245, 235.

ESI-MS: m/z 1032.5 Th $[C_{66}H_{78}N_7O_4]^+$.

Step e) Synthesis of 5,10,15-tris-[4-(2-N,N,N-trimethylammonium)ethoxyphenyl]-20-[(4-decyloxy) phenyl]porphyrin triiodide To a solution of 5,10,15-tris-[4-(2-N,N-dimethylaminoethoxy)phenyl]-20-[(4-decyloxy)phenyl]porphyrin (15 mg, 0.015 mmol) in dry NMP (5 ml), iodomethane (100 mg, 0.6 mmol) was added. The reaction mixture was kept under magnetic stirring, at room temperature, for 20 hours, then diethyl ether was added slowly until a precipitate appeared. The suspension was filtered and the solid crystallized from MeOH/diethyl ether to give 20 mg of pure product of the title (yield 94%).

$^1$H NMR (300 MHz, DMSO-d$^6$): 8.16 (6H, m), 8.08 (2H, m), 7.45 (6H, m), 7.35 (2H, m), 4.76 (6H, m), 4.25 (2H, t, J=6 Hz), 3.97 (6H, m), 3.32 (27H, s), 1.88 (2H, m), 1.56-1.28 (14H, m), 0.86 (3H, t, J=6.3 Hz); −2.91 (2H, s).

$^{13}$C NMR (75 MHz, DMSO-d$^6$, selected data): 158.0, 136.1, 134.9, 131.9, 120.1, 113.9, 113.7, 68.3, 65.0, 62.55, 53.9, 31.9, 29.6, 29.5, 29.4, 29.3, 26.2, 22.7, 14.5.

UV-VIS (DMF): $\lambda_{max}$ 650, 554, 517, 431, 400, 254, 245, 234.

ESI-MS: m/z 358.8 Th $[C_{69}H_{86}N_7O_4]^{3+}$.

Step b1) Synthesis of 2-[4-(di-1H-pyrrol-2-ylmethyl)phenoxy]ethanol

To a solution of 4-(2-hydroxyethoxy)benzaldehyde (664 mg, 4 mmol) in pyrrole (12.5 ml, 180 mmol), TFA (114 mg, 1 mmol) was added. The reaction mixture was kept under magnetic stirring, at room temperature, for 1 hour, then ethyl acetate (200 ml) was added and the solution washed with $NaHCO_3$ saturated solution, then the organic phase was dried with $Na_2SO_4$. After evaporation, the crude product was purified by chromatography (Petroleum ether/Ethyl acetate 1/1). 811 mg (yield 72%) of the title product were obtained.

$^1$H NMR (300 MHz, CDCl$_3$): 7.94 (2H, bs), 7.13 (2H, m), 6.87 (2H, m), 6.69 (2H, m), 6.15 (2H, m), 5.91 (2H, m), 5.91 (1H, s), 4.07 (2H, dt, J=9, 4.5 Hz), 3.95 (2H, dt, J=9, 7.5 Hz).

$^{13}$C NMR (75 MHz, CDCl$_3$): 157.6, 134.7, 132.7, 129.5, 117.1, 114.6, 108.4, 107.0, 69.1, 61.4, 43.1.

Step c1) Synthesis of 5,10,15-tris-[4-(2-hydroxyethoxy)phenyl]-20-[(4-decyloxy)phenyl]porphyrin To a solution of 2-[4-(di-1H-pyrrol-2-ylmethyl)phenoxy] ethanol (620 mg, 2.2 mmol, 4-decyloxybenzaldehyde (262 mg, 1 mmol) and 4-(2-hydroxyethoxy)benzaldehyde (166 mg, 1.4 mmol) in dry $CH_2Cl_2$, trifluoroacetic acid (114 mg, 1 mmol) was added and the mixture was kept under magnetic stirring, at room temperature, under nitrogen atmosphere, for 4 hours. Then p-chloranil (492 mg, 2 mmol) was added and the final mixture stirred for additional 15 hours, then the organic phase was washed with $Na_2CO_3$ saturated solution, dried on $Na_2SO_4$ and the solvent removed by evaporation. The crude product was purified by chromatography on silica gel (THF/Petroleum ether 1/1+1% TEA, to THF+1% TEA), to give 35 mg of title product (yield 3.7%).

According to the procedures described in Examples 1 or 2 the following porphyrins have been prepared:

EXAMPLE 3

5,10,15-tris-{[4-(N-methylpiperidin-4-yl)oxy]phenyl}-20-[(4-decyloxy) phenyl]porphyrin ESI-MS: m/z 1110.5 Th $[C_{72}H_{84}N_7O_4]^+$

EXAMPLE 4

5,10,15-tris-{[4-(N,N-dimethylpiperidin-4-ium)oxy]phenyl}-20-[(4-decyloxy)phenyl]porphyrin triiodide ESI-MS: m/z 385.2 Th $[C_{75}H_{92}N_7O_4]^{3+}$

EXAMPLE 5

5,10,15-tris-[3-(2-morpholin-4-ylethoxy)phenyl]-20-[(4-decyloxy)phenyl]porphyrin ESI-MS: m/z 1158.8 Th $[C_{72}H_{84}N_7O_7]^+$

EXAMPLE 6

5,10,15-tris-{[3-(2-methylmorpholin-4-ium)ethoxy]phenyl}-20-[(4-decyloxy)phenyl]porphyrin triiodide ESI-MS: m/z 400.9 Th $[C_{75}H_{92}N_7O_7]^{3+}$

EXAMPLE 7

5,10,15-tris-{4-[4-(N,N-dimethylamino)phenoxy]phenyl}-20-[(4-decyloxy)Phenyl]porphyrin ESI-MS: m/z 1176.6 Th $[C_{78}H_{78}N_7O_4]^+$

EXAMPLE 8

5,10,15-tris-{4-[4-(N,N,N-trimethylammonium)phenoxy]phenyl}-20-[(4-decyloxy)phenyl]porphyrin triiodide ESI-MS: m/z 406.8 Th $[C_{81}H_{86}N_7O_4]^{3+}$

EXAMPLE 9

5,10,15-tris-{4-[3-(N,N-dimethylamino)phenyl]thiophenyl}-20-[(3-undecyloxy)phenyl]porphyrin ESI-MS: m/z 1239.7 Th $[C_{79}H_{80}N_7OS_3]^+$

EXAMPLE 10

5,10,15-tris-{4-[3-(N,N,N-trimethylammonium)phenyl]thiophenyl}-20-[(4-undecyloxy)phenyl]porphyrin triiodide ESI-MS: m/z 427.7 Th $[C_{82}H_{88}N_7OS_3]^{3+}$

EXAMPLE 11

5,10,15-tris-[3-(3-N,N-dimethylaminopropoxy)phenyl]-20-[(3-undecyloxy)phenyl]porphyrin ESI-MS: m/z 1088.6 Th $[C_{70}H_{86}N_7O_4]^+$

EXAMPLE 12

5,10,15-tris-[3-(3-N,N,N-trimethylammoniumpropoxy)phenyl]-20-[(3-undecyloxy)phenyl]porphyrin triiodide ESI-MS: m/z 377.7 Th $[C_{73}H_{94}N_7O_4]^{3+}$

EXAMPLE 13

5,10,15-tris-{4-[4-(N,N-dimethylamino)butoxy]phenyl]-20-[(4-undecyloxy)phenyl]porphyrin ESI-MS: m/z 1131.6 Th $[C_{73}H_{92}N_7O_4]^+$

EXAMPLE 14

5,10,15-tris-{4-[4-(N,N,N-trimethylammonium)butoxy]phenyl}-20-[(4-undecyloxy)phenyl]porphyrin triiodide ESI-MS: m/z 379.7 Th $[C_{76}H_{100}N_7O_4]^{3+}$

EXAMPLE 15

5-{4-{2,4,6-tris-[(dimethylamino)methyl]phenoxy}phenyl}-10,15,20-tris-[(4-decyloxy)phenyl]porphyrin ESI-MS: m/z 1346.9 Th $[C_{89}H_{116}N_7O_4]^+$

EXAMPLE 16

5-{4-{2,4,6-tris-[(trimethylammonium)methyl]phenoxy}phenyl}-10,15,20-tris-[(4-decyloxy)phenyl]porphyrin triiodide
ESI-MS: m/z 463.6 Th $[C_{92}H_{124}N_7O_4]^{3+}$

EXAMPLE 17

5-{3-[2-(dimethylamino)]-1-{[(dimethylamino)methyl]ethoxy}phenyl}-10,15,20-tris-[(3-decyloxy)phenyl]porphyrin
ESI-MS: m/z 1227.8 Th $[C_{81}H_{107}N_6O_4]^+$

EXAMPLE 18

5-{3-[2-(trimethylammonium)-1-(trimethylammonium)methyl]ethoxy}phenyl}-10,15,20-tris-[(3-decyloxy)phenyl]porphyrin diiodide ESI-MS: m/z 628.4 Th $[C_{83}H_{112}N_6O_4]^{2+}$

EXAMPLE 19

5,10,15-tris-{4-[3-(diethylamino)propoxy]phenyl}-20-[(4-decyloxy)phenyl]porphyrin ESI-MS: m/z 1172.7 Th $[C_{76}H_{98}N_7O_4]^+$

EXAMPLE 20

5,10,15-tris-{4-[3-(trimethylammonium)propoxy]phenyl}-20-[(4-decyloxy)phenyl]porphyrin triiodide ESI-MS: m/z 419.6 Th $[C_{82}H_{112}N_7O_4]^{3+}$

EXAMPLE 21

5,10,15-tris-[4-(2-aminoethoxy)phenyl]-20-[(4-decyloxy)phenyl]porphyrin

ESI-MS: m/z 962.5 Th $[C_{61}H_{68}N_7O_4]^+$

EXAMPLE 22

5,10,15-tris-{[4-(2-trimethylammonium)ethoxy]phenyl}-20-[(4-decyloxy)phenyl]porphyrin triiodide ESI-MS: m/z 363.5 Th $[C_{70}H_{88}N_7O_4]^{3+}$

EXAMPLE 23

5,10,15-tris-{{[4-(N,N,N-trimethylammonium)phenoxy]carbonyl}phenyl}-20-[(4-decyloxy)phenyl]porphyrin triiodide ESI-MS: m/z 434.6 Th $[C_{84}H_{86}N_7O_7]^{3+}$

EXAMPLE 24

5-{4-{{2-(trimethylammonium)-1-[(trimethylammonium)methyl]ethoxy}carbonyl}phenyl}-10,15,20-tris-[(3-decyloxy)phenyl]porphyrin diiodide ESI-MS: m/z 1270.8 Th $[C_{83}H_{110}N_6O_5]^+$

EXAMPLE 25

Synthesis of 5,15-bis-[3-(3-N,N,N-trimethylammoniumpropoxy)phenyl]porphyrin diiodide

Step a) Synthesis of 2-(1H-pyrrol-2-ylmethyl)-1H-pyrrole (dipyrromethane)

To a solution of p-formaldehyde (1100 mg, 35 mmol) in pyrrole (50 ml, 720 mmol), at 50° C., TFA (416 mg, 3.5 mmol) was added. The reaction mixture was kept under magnetic stirring, at room temperature, for 30 minutes, then ethyl acetate was added and the solution washed with NaHCO$_3$ saturated solution, then the organic phase was dried on Na$_2$SO$_4$. After evaporation the crude product was purified by chromatography on silica gel (Petroleum Ether/Ethyl acetate 4/1+1% TEA). 1950 mg (yield 38%) of the product were obtained.

$^1$H NMR (300 MHz, DMSO-d$^6$): 6.55 (2H, m), 5.85 (2H, m), 5.71 (2H, m), 3.78 (2H, s).
$^{13}$C NMR (75 MHz, CDCl$_3$): 129.0, 117.3, 108.3, 106.4, 26.2.

Step b) Synthesis of 3-(3-hydroxypropoxy)benzaldehyde

To a solution of 3-hydroxybenzaldehyde (366 mg, 3 mmol) in anhydrous DMF (7 ml), under nitrogen atmosphere, K$_2$CO$_3$ (829 mg, 6 mmol), and, after 10 minutes, 3-bromo-1-propanol (500 mg, 3.6 mmol) were added. The mixture was heated to reflux for 2 hours, then water was added and the product was extracted with CH$_2$Cl$_2$. The organic layers were washed with water and with NaCl saturated solution, dried on Na$_2$SO$_4$. After evaporation of the solvent the crude product was purified by chromatography on silica gel (Petroleum ether/Ethyl acetate 2/1); 520 mg (yield 95%) of title product were obtained.

$^1$H NMR (300 MHz, CDCl$_3$): 9.95 (1H, s), 7.43 (2H, m), 7.38 (1H, d, J=1.8 Hz), 7.17 (1H, m), 4.17 (2H, t, J=6 Hz), 3.86 (2H, t, J=6 Hz), 2.06 (2H, tt, J=6 Hz, 6 Hz).
$^{13}$C NMR (75 MHz, CDCl$_3$): 192.1, 159.3, 137.7, 130.1, 123.6, 121.8, 112.8, 65.7, 60.0, 31.8.

Step c) Synthesis 5,15-bis-[3-(3-hydroxypropoxy)phenyl]porphyrin

To a solution of 2-(1H-pyrrol-2-ylmethyl)-1H-pyrrole (236 mg, 1.6 mmol) and 3-(3-hydroxypropoxy)benzaldehyde (305 mg, 1.6 mmol) in dry CH$_2$Cl$_2$ (160 ml), trifluoroacetic acid (114 mg, 1 mmol) was added and the mixture was kept under magnetic stirring, at room temperature, under nitrogen atmosphere, for 4 hours. Then p-chloranil (492 mg, 2 mmol) was added and the final mixture stirred for additional 5 hours, then the organic phase was washed with Na$_2$CO$_3$ saturated solution, dried on Na$_2$SO$_4$ and the solvent removed by evaporation. The crude product was purified by chromatography on silica gel (CHCl$_3$/MeOH 97/3), to give 100 mg of title product (yield 20%).

$^1$H NMR (300 MHz, CDCl$_3$): 10.32 (2H, s), 9.39 (4H, d, J=4.2 Hz), 9.12 (4H, d, J=4.2 Hz), 7.85 (4H, m), 7.69 (2H, dd, J=8.4 Hz, 7.5 Hz), 7.36 (2H, dd, J=8.4 Hz, 2.0 Hz), 4.36 (4H, t, J=6.0 Hz), 3.96 (4H, t, J=6.0 Hz), 2.16 (4H, tt, J=6.0 Hz, 6.0 Hz), −3.15 (2H, s).
$^{13}$C NMR (75 MHz, CDCl$_3$): 157.3, 146.9, 145.2, 142.7, 131.6, 131.0, 128.0, 127.8, 121.2, 118.7, 114.0, 105.2, 65.9, 60.5, 32.0.

Step d) Synthesis of 5,15-bis-[3-(3-methylsulphonylpropoxy)phenyl]porphyrin

To a solution of 5,15-bis-[3-(3-hydroxypropoxy)phenyl]porphyrin (30 mg, 0.049 mmol) in anhydrous CH$_2$Cl$_2$, under nitrogen atmosphere, at 0° C., triethylamine (29 mg mg, 0.29 mmol) and methansulphonylchloride (17 mg, 0.15 mmol) were added. The mixture was kept under magnetic stirring at 0° C. for 3 hours, then washed with NaHCO$_3$ saturated solution and with water. The organic phase was dried under Na$_2$SO$_4$ and the solvent removed by evaporation. The crude product was purified by chromatography on silica gel (CHCl$_3$), to obtain 17 mg of the pure title product (yield 45%).

$^1$H NMR (300 MHz, CDCl$_3$): 10.33 (2H, s), 9.40 (4H, d, J=4.8 Hz), 9.12 (4H, d, J=4.8 Hz), 7.90 (2H, d, J=7.5 Hz), 7.82 (2H, s), 7.70 (2H, dd, J=8.4 Hz, 7.5 Hz), 7.35 (2H, d, J=8.4 Hz), 4.54 (4H, t, J=6.3 Hz), 4.32 (4H, t, J=5.7 Hz), 3.02 (6H, s), 2.34 (4H, tt, J=6.3 Hz, 5.7 Hz), −3.14 (2H, bs).
$^{13}$C NMR (75 MHz, DMSO-d$^6$): 157.8, 147.0, 145.5, 142.5, 133.3, 131.5, 128.9, 128.4, 121.7, 119.0, 115.0, 106.4, 98.8, 68.1, 64.6, 37.2, 29.3.
ESI-MS: m/z 767.5 Th $(C_{40}H_{39}N_4O_8S_2)^+$

Step e) Synthesis of 5,15-bis-[3-(3-N,N-dimethylaminopropoxy))phenyl]porphyrin To a solution of 5,15-bis[3-(3-methylsulphonylpropoxy)phenyl]porphyrin (15 mg, 0.019 mmol) in anhydrous DMF (2 ml), under nitrogen atmosphere, K$_2$CO$_3$ (14 mg, 0.11 mmol), and, after 10 minutes, dimethylamine hydrochloride (8 mg, 0.11 mmol) were added. The mixture was heated at 80° C. for 15 hours, then water was added and the product was extracted with CH$_2$Cl$_2$. The organic layers were washed with water and with NaCl saturated solution, dried on Na$_2$SO$_4$. After evaporation the crude product was purified by flash chromatography (THF to THF/DMF 9/1). After the chromatography, the product was washed with CHCl$_3$/Petroleum Ether 1/1 and 10 mg (yield 80%) of pure title product were obtained.

$^1$H NMR (300 MHz, D$_2$O+HCl): 10.83 (2H, s), 9.40 (4H, m), 8.95 (4H, m), 7.83 (4H, m), 7.74 (2H, m), 3.38 (4H, m), 3.30 (4H, m), 2.78 (12H, s), 2.19 (4H, m).

$^{13}$C NMR (75 MHz, D$_2$O+HCl, selected data): 157.7, 145.1, 142.4, 139.8, 131.8, 130.6, 130.3, 129.7, 124.4, 112.1, 116.5, 106.9, 65.7, 55.6, 43.0, 24.3.

ESI-MS: m/z 665.6 Th (C$_{42}$H$_{45}$N$_6$O$_2$)$^+$

Step f) Synthesis of 5,15-bis-[3-(3-N,N,N-trimethylammonium) propoxyphenyl]porphyrin diiodide To a solution of 5,15-bis-[3-(3-N,N-dimethylaminopropoxy)phenyl]porphyrin (26 mg, 0.039 mmol) in dry NMP (5 ml), iodomethane (110 mg, 0.78 mmol) was added. The reaction mixture was kept under magnetic stirring, at room temperature, for 24 hours, then diethyl ether was added slowly until a precipitate appeared. The suspension was filtered and the solid crystallized from MeOH/diethyl ether to give 26 mg of pure title product (yield 70%).

$^1$H NMR (300 MHz, DMSO-d$^6$): 10.64 (2H, s), 9.66 (4H, d, J=4.6 Hz), 9.07 (4H, d, J=4.6 Hz), 7.86 (4H, m), 7.80 (2H, dd, J=8.1 Hz, 7.0 Hz), 7.48 (2H, d, J=7.0 Hz), 4.32 (4H, t, J=5.7 Hz), 3.58 (4H, m), 3.10 (18H, s), 2.29 (4H, m), –3.29 (2H, s).

$^{13}$C NMR (75 MHz, DMSO-d$^6$, selected data): 157.5, 146.8, 145.3, 142.3, 133.0, 131.2, 128.8, 121.6, 118.7, 114.8, 108.6, 106.2, 65.6, 63.6, 52.8, 23.1.

UV-VIS (DMF): $\lambda_{max}$ 670, 629, 575, 535, 500, 381, 256, 244.

ESI-MS: m/z 347.4 Th (C$_{44}$H$_{50}$N$_6$O$_2$)$^{2+}$

According to the procedures described in Example 25 the following porphyrins have been prepared:

EXAMPLE 26

5,15-bis-[4-(2-piperidin-1-ylethoxy)phenyl]porphyrin

ESI-MS: m/z 717.4 Th (C$_{46}$H$_{49}$N$_6$O$_2$)$^+$

EXAMPLE 27

5,15-bis-[4-(2-N-methylpiperidin-1-iumethoxy)phenyl]porphyrin diiodide

ESI-MS: m/z 373.2 Th (C$_{48}$H$_{54}$N$_6$O$_2$)$^{2+}$

EXAMPLE 28

5,15-bis-[4-(3-N,N-dimethylaminopropoxy)phenyl]-10,20-bis-[(3-decyloxy)phenyl]porphyrin ESI-MS: m/z 1129.7 Th (C$_{74}$H$_{93}$N$_6$O$_4$)$^+$

EXAMPLE 29

5,15-bis-[4-[3-N,N,N-trimethylammoniumpropoxy) phenyl]-10,20-bis-[(3-decyloxy)phenyl]porphyrin diiodide ESI-MS: m/z 579.3 Th (C$_{76}$H$_{98}$N$_6$O$_4$)$^{2+}$

EXAMPLE 30

5,15-bis 4-{[2-(N,N-dimethylamino)ethylthio]phenyl}porphyrin

ESI-MS: m/z 669.39 Th (C$_{40}$H$_{41}$N$_6$S$_2$)$^+$

EXAMPLE 31

5,15-bis-{4-[2-(N,N,N-trimethylammonium)ethylthio]phenyl}porphyrin diiodide

ESI-MS: m/z 349.4 Th (C$_{42}$H$_{46}$N$_6$S$_2$)$^{2+}$

EXAMPLE 32

5,15-bis-{4-{2-[3-(trimethylammonium)phenoxy]ethoxy}phenyl}porphyrin diiodide

ESI-MS: m/z 425.2 Th (C$_{54}$H$_{54}$N$_6$O$_4$)$^{2+}$

EXAMPLE 33

5,15-bis-{4-{2-[3-(N,N,N-trimethylammonium)phenyl]-2-oxoethyl}-10,20-bis-[(3-decyloxy)phenyl]porphyrin diiodide ESI-MS: m/z 639.4 Th (C$_{86}$H$_{98}$N$_6$O$_4$)$^{2+}$

EXAMPLE 34

Synthesis of 5,15-bis-[3-(3-N,N,N-trimethylammoniumpropoxy)phenyl]porphyrinate zinc(II) diiodide Step a) Synthesis of 5,15-bis-[3-(3-hydroxypropoxy)phenyl]porphyrinate zinc(II)

To a solution of 5,15-bis-[3-(3-hydroxypropoxy)phenyl] porphyrin (100 mg, 0.16 mmol) in CHCl$_3$/THF 1/1 (10 ml), zinc acetate (183 mg, 1 mmol) was added and the mixture was kept under magnetic stirring, at 40° C., under nitrogen for 4 hours. Then the solid was filtered through celite and the liquid phase was dried on Na$_2$SO$_4$, then the solvent removed by evaporation to obtain 110 mg of title product (yield 98%) that was used in the following step without further purification.

$^1$H NMR (300 MHz, CDCl$_3$): 10.24 (2H, s), 9.35 (4H, d, J=4.5 Hz), 9.08 (4H, d, J=4.5 Hz), 7.81 (2H, d, J=8.1 Hz), 7.63 (2H, s), 7.58 (2H, dd, J=8.1 Hz, 7.5 Hz), 7.12 (2H, d, J=7.5 Hz), 3.96 (4H, m), 3.25 (4H, m), 1.66 (4H, m).

$^{13}$C NMR (75 MHz, CDCl$_3$): 156.9, 149.9, 149.7, 144.0, 132.4, 131.7, 127.9, 127.3, 121.0, 119.5, 113.7, 106.1, 65.9, 60.3, 31.7.

Step b) Synthesis of 5,15-bis-[3-(3-methylsulphonylpropoxy)phenyl]porphyrinate zinc(II)

To a solution of 5,15-bis-[3-(3-hydroxypropoxy)phenyl] porphyrinate zinc (100 mg, 0.14 mmol) in anhydrous CH$_2$Cl$_2$, under nitrogen atmosphere, at 0° C., triethylamine (43 mg mg, 0.42 mmol) and methansulphonylchloride (36 mg, 0.31 mmol) were added. The mixture was kept under magnetic stirring at 0° C. for 2 hours, then washed with NaHCO$_3$ saturated solution and with water. The organic phase was dried on Na$_2$SO$_4$ and the solvent removed by evaporation. The crude product was purified by flash chromatography on silica gel (CHCl$_3$/MeOH 99/1), to obtain 70 mg of the pure title product (yield 60%).

$^1$H NMR (300 MHz, CDCl$_3$): 10.33 (2H, s), 9.44 (4H, d, J=4.5 Hz), 9.17 (4H, d, J=4.5 Hz), 7.89 (2H, d, J=7.8 Hz), 7.82 (2H, s), 7.69 (2H, dd, J=8.1 Hz, 7.8 Hz), 7.35 (2H, d, J=8.1 Hz), 4.53 (4H, t, J=6.0 Hz), 4.31 (4H, t, J=6 Hz), 3.02 (6H, s), 2.33 (4H, tt, J=6.0 Hz, 6.0 Hz).

$^{13}$C NMR (75 MHz, CDCl$_3$): 156.9, 149.9, 149.5, 144.0, 132.5, 131.8, 128.0, 127.6, 121.0, 119.6, 113.8, 106.3, 66.8, 63.4, 37.2, 29.2.

APCl-MS: m/z 829.1 Th (C$_{40}$H$_{39}$N$_4$O$_8$S$_2$Zn)$^+$

Step c) Synthesis of 5,15-bis-[3-(3-N,N-dimethylaminopropoxy))phenyl]porphyrinate zinc(II)

To a solution of 5,15-bis-[3-(3-methylsulphonylpropoxy) phenyl]porphyrinate zinc (15 mg, 0.019 mmol) in anhydrous DMF (2 ml), under nitrogen atmosphere, K$_2$CO$_3$ (14 mg, 0.11 mmol), and, after 10 minutes, dimethylamine hydrochloride (8 mg, 0.11 mmol) were added. The mixture was heated at 80° C. for 15 hours, then water was added and the product was extracted with CH$_2$Cl$_2$. The organic layers were washed with water and with NaCl saturated solution, then dried on Na$_2$SO$_4$. After evaporation the crude product was purified by chromatography (THF to THF/DMF 9/1). After the chromatography, the product was washed with CHCl$_3$/Petroleum Ether 1/1 and 10 mg (yield 80%) of pure product of the title were obtained.

$^1$H NMR (300 MHz, D$_2$O+HCl): 11.16 (2H, s), 9.67 (4H, d, J=4.5 Hz), 9.17 (4H, m), 8.05 (2H, d, J=9.0 Hz), 7.82 (2H, dd, J=9.0 Hz, 8.4 Hz), 7.51 (2H, d, J=8.4 Hz), 4.32 (4H, m), 3.35 (4H, t, J=8.2 Hz), 2.82 (12H, s), 2.23 (4H, m).

$^{13}$C NMR (75 MHz, D$_2$O+HCl, selected data): 157.8, 145.5, 142.8, 140.1, 131.9, 131.0, 129.6, 124.8, 121.5, 116.5, 107.1, 65.8, 55.7, 43.0, 24.3.

UV-VIS (DMF): $\lambda_{max}$ 544, 406, 310, 255, 244.

APCl-MS: m/z 727.0 Th (C$_{42}$H$_{45}$N$_6$O$_2$Zn)$^+$

Step d) Synthesis of 5,15-bis-[3-(3-N,N,N-trimethylammoniumpropoxy)phenyl]porphyrinate zinc(II) diiodide To a solution of 5,15-bis-[3-(3-N,N-dimethylaminopropoxy)phenyl]porphyrinate zinc (64 mg, 0.088 mmol) in dry NMP (5 ml), iodomethane (374 mg, 2.63 mmol) was added. The reaction mixture was kept under magnetic stirring, at room temperature, for 24 hours, then diethyl ether was added slowly until a precipitate appeared. The suspension was filtered and the solid crystallized from MeOH/diethyl ether to give 70 mg of pure title product (yield 80%).

$^1$H NMR (300 MHz, DMSO-d$^6$): 10.35 (2H, s), 9.48 (4H, d, J=4.2 Hz), 8.98 (4H, d, J=4.2 Hz), 7.79 (4H, m), 7.73 (2H, dd, J=9.3 Hz, 7.0 Hz), 7.42 (2H, d, J=9.3 Hz), 4.31 (4H, t, J=6.0 Hz), 3.57 (4H, m), 3.10 (18H, s), 2.48 (4H, m).

$^{13}$C NMR (75 MHz, DMSO-d$^6$, selected data): 157.3, 149.7, 149.6, 132.8, 132.3, 128.3, 121.7, 119.2, 114.3, 106.8, 65.7, 63.7, 52.9, 23.4.

UV-VIS (DMF): $\lambda_{max}$ 544, 408, 392, 312, 264.

ESI-MS: m/z 347.4 Th (C$_{44}$H$_{50}$N$_6$O$_2$Zn)$^{2+}$

EXAMPLE 35

Synthesis of 5,15-bis-[4-(4-N,N,N-trimethylammoniumphenoxy)phenyl]porphyrin diiodide Step a) Synthesis of 4-(4-nitrophenoxy)benzaldehyde To a solution of 4-hydroxybenzaldehyde (366 mg, 3 mmol) in anhydrous DMF (7 ml), under nitrogen atmosphere, K$_2$CO$_3$ (829 mg, 6 mmol), and, after 10 minutes, 4-bromonitrobenzene (726 mg, 3.6 mmol) were added. The mixture was heated to reflux for 3 hours, then water was added and the product was extracted with CH$_2$Cl$_2$. The organic layers were washed with water and with NaCl saturated solution and dried with Na$_2$SO$_4$. After evaporation of the solvent the crude product was purified by chromatography on silica gel (Petroleum ether/Ethyl acetate 5/1); 605 mg (yield 82%) of pure title product were obtained.

$^1$H NMR (300 MHz, CDCl$_3$): 9.99 (1H, s), 8.27 (2H, m), 7.94 (2H, m), 7.20 (2H, m), 7.14 (2H, m).

$^{13}$C NMR (75 MHz, CDCl$_3$): 190.7, 161.5, 160.6, 133.2, 132.3, 126.3, 119.9, 119.0.

Step c) Synthesis of 5,15-bis-[4-(4-nitrophenoxy)phenyl]porphyrin

To a solution of 2-(1H-pyrrol-2-ylmethyl)-1H-pyrrole (200 mg, 1.37 mmol) and 4-(4-nitrophenoxy)benzaldehyde (305 mg, 1.6 mmol) in dry CH$_2$Cl$_2$ (130 ml), trifluoroacetic acid (114 mg, 1 mmol) was added and the mixture was kept under magnetic stirring, at room temperature, under nitrogen atmosphere for 3 hours, then p-chloranil (492 mg, 2 mmol) was added and the final mixture stirred for additional 15 hours, then the organic phase was washed with Na$_2$CO$_3$ saturated solution, dried with Na$_2$SO$_4$ and the solvent removed by evaporation. The crude product was purified by chromatography on silica gel (CHCl$_3$/Petroleum ether 3/1), to give 45 mg of title product (yield 10%).

$^1$H NMR (300 MHz, CDCl$_3$): 10.37 (2H, s), 9.45 (4H, d, J=4.5 Hz), 9.12 (4H, d, J=4.5 Hz), 8.41 (4H, m), 8.34 (4H, m), 7.54 (4H, m), 7.41 (4H, m), −3.11 (2H, bs).

$^{13}$C NMR (75 MHz, CDCl$_3$, selected data): 154.9, 147.1, 145.3, 140.1, 138.4, 136.4, 132.0, 130.8, 128.6, 126.3, 126.2, 118.9, 117.7, 105.6.

UV-VIS (DMF): $8_{max}$ 629, 574, 535, 409, 395, 382, 305, 249, 233.

ESI-MS: m/z 737.3 Th (C$_{44}$H$_{29}$N$_6$O$_6$)$^+$

Step d) Synthesis of 5,15-bis-[4-(4-aminophenoxy)phenyl]porphyrin

To a solution of 5,15-bis-[4-(4-nitrophenoxy)phenyl]porphyrin (70 mg, 0.095 mmol) in CHCl$_3$ (10 ml), saturated with concentrated HCl, SnCl$_2$.2H$_2$O (105 mg, 0.475 mmol) was added and the mixture was kept under magnetic stirring, at room temperature for 24 h, then cold water was added, the mixture was neutralized with a solution 15% of ammonia, and the organic phase was extracted, dried on Na$_2$SO$_4$, then the solvent was removed by evaporation. The crude product was purified by chromatography on silica gel (THF to THF/DMF 9/1), to give 43 mg of title product (yield 67%).

$^1$H NMR (300 MHz, CDCl$_3$): 10.31 (2H, s), 9.40 (4H, d, J=4.8 Hz), 9.12 (4H, d, J=4.8 Hz), 8.16 (4H, m), 7.35 (4H, m), 7.21 (4H, m), 6.86 (4H, m), −3.10 (2H, s).

$^{13}$C NMR (75 MHz, CDCl$_3$, selected data): 159.1, 148.5, 147.4, 145.1, 136.5, 135.9, 131.6, 131.0, 126.2, 121.7, 118.9, 117.7, 116.4, 115.5, 105.2.

UV-VIS (DMF): $\lambda_{max}$ 630, 576, 536, 501, 382, 265, 253.

ESI-MS: m/z 677.3 Th (C$_{44}$H$_{33}$N$_6$O$_2$)$^+$

Step f) Synthesis of 5,15-bis-[(4-(4-N,N,N-trimethylammoniumphenoxy) phenyl]porphyrin diiodide To a solution of 5,15-bis-[4-(4-aminophenoxy)phenyl] porphyrin (30 mg, 0.042 mmol) in dry NMP (5 ml), iodomethane (150 mg, 1.1 mmol) was added. The reaction mixture was kept under magnetic stirring, at room temperature, for 24 hours, then diethyl ether was added slowly until a precipitate appeared. The suspension was filtered and the solid crystallized from MeOH/diethyl ether to give 35 mg of pure title product (yield 80%).

$^1$H NMR (300 MHz, DMSO-d$^6$): 10.66 (2H, s), 9.71 (4H, d, J=4.8 Hz), 9.12 (4H, d, J=4.8 Hz), 8.35 (4H, m), 8.14 (4H, m), 7.58 (8H, m), 3.68 (18H, m), −3.27 (2H, s).

$^{13}$C NMR (75 MHz, DMSO-d$^6$, selected data): 156.3, 147.1, 142.9, 136.8, 133.2, 131.4, 123.3, 120.0, 118.5, 115.3, 111.2, 106.4, 98.6, 57.2.

UV-VIS (DMF): $\lambda_{max}$ 577, 539, 502, 392, 265, 254, 244, 235.

ESI-MS: m/z 381.3 Th $(C_{50}H_{46}N_6O_2)^{2+}$

According to the procedures described in Example 35 the following porphyrins have been prepared:

EXAMPLE 36

5,15-bis-[3-(4-N,N-dimethylaminophenoxy)phenyl] porphyrin

ESI-MS: m/z 733.3 Th $(C_{48}H_{41}N_6O_2)^+$

EXAMPLE 37

5,15-bis-[3-(4-N,N,N-trimethylammoniumphenoxy) phenyl]porphyrin diiodide

ESI-MS: m/z 381.2 Th $(C_{50}H_{46}N_6O_2)^{2+}$

EXAMPLE 38

5,15-bis-[3-(4-N,N-dimethylaminophenyl)thiophenyl]porphyrin

ESI-MS: m/z 765.3 Th $(C_{48}H_{41}N_6S_2)^+$

EXAMPLE 39

5,15-bis-[3-(4-N,N,N-trimethylammoniumthiophenoxy)phenyl]porphyrin diiodide

ESI-MS: m/z 795.3 Th $(C_{48}H_{41}N_6O_2)^{2+}$

EXAMPLE 40

5,15-bis-4-[3-(N,N-dimethylaminophenoxy)phenyl]-10,20-bis-[(4-decyloxy)phenyl]porphyrin ESI-MS: m/z 1197.6 Th $(C_{80}H_{89}N_6O_4)^{2+}$

EXAMPLE 41

5,15-bis-4-[3-(N,N,N-trimethylammoniumphenoxy) phenyl]-10,20-bis-[(4-decyloxy)phenyl]porphyrin diiodide ESI-MS: m/z 795.3 Th $(C_{82}H_{94}N_6O_4)^{2+}$ According with the procedure reported in Examples 1 and 34 or by metallation of metal free porphyrins, the following Zn(II)-porphyrinates have been prepared:

EXAMPLE 42

5,10,15-tris-{4-[4-(N,N-dimethylamino)butoxy]phenyl}-20-[(4-undecyloxy)phenyl]porphyrinate zinc(II)

ESI-MS: m/z 1194.9 Th $[C_{73}H_{90}N_7O_4Zn]^+$

EXAMPLE 43

5,10,15-tris-{4-[4-(N,N,N-trimethylammonium)butoxy]phenyl}-20-[(4-undecyloxy)phenyl]porphyrinate zinc(II) triiodide ESI-MS: m/z 418.3 Th $[C_{77}H_{102}N_7O_4Zn]^{3+}$

EXAMPLE 44

5,15-bis-[4-(2-piperidin-1-ylethoxy)phenyl]porphyrinate zinc(II)

ESI-MS: m/z 780.3 Th $(C_{46}H_{47}N_6O_2Zn)^+$

EXAMPLE 45

5,15-bis-[4-(2-N-methylpiperidin-1-iumethoxy)phenyl]porphyrinate zinc(II) diiodide ESI-MS: m/z 405.2 Th $(C_{48}H_{52}N_6O_2Zn)^{2+}$

The invention claimed is:

1. A method of treating infectious diseases of fungine or bacterial origin, comprising: administering to a patient having a pathologically affected tissue and in need of such a treatment an effective amount of at least a compound of general formula (I)

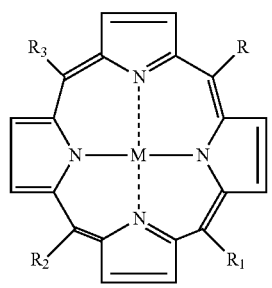

(I)

wherein
R is the following group of formula (II)

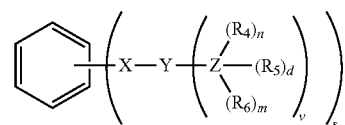

(II)

wherein
X is selected from the group consisting of O, S, $CH_2$, COO, $CH_2CO$, $O(CH_2)_2O$, $O(CH_2)_3O$ and N;

Z is selected from between N and $CH_2N$;

Y is selected from aliphatic groups, linear or branched, saturated or unsaturated, having from 1 to 10 carbon atoms, and phenyl, or Y forms with Z a saturated or unsaturated heterocycle, selected from the group consisting of: morpholine, piperidine, pyrimidine, piperazine, pyrrolidine, pyrroline, julolidine (2,3,6,7-tetrahydro-1H,5H-pirido[3,2,1-Ij]quinoline, and substituted forms thereof;

$R_4$ and $R_5$, equal or different from each other, are selected from H and alkyl groups having from 1 to 3 carbon atoms, or they form with the Z group a saturated or unsaturated heterocycle, selected from the group consisting of: morpholine, piperidine, pyrimidine, piperazine, pyrrolidine, pyrroline, julolidine (2,3,6,7-tetrahydro-1H,5H-pirido[3,2,1-Ij]quinoline), and substituted forms thereof;

$R_6$ is selected from H and aliphatic groups, linear or branched, saturated or unsaturated, having from 1 to 5 carbon atoms, comprising a saturated heterocycle selected from the group consisting of:

morpholine, piperidine, piperazine, pyrrolidine, and substituted forms thereof;

d, m, and n, equal of different from each other, are selected from 0 and 1;

v and s, equal or different from each other, are integers comprised between 1 and 3;

$R_1$ is selected from H and a group of formula (III)

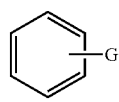

(III)

wherein

G is selected from H and $P-(CH_2)_l-(W)_f-J$, wherein

P is selected from the group consisting of O, $CH_2$, $CO_2$, NHCONH and CONH;

l is an integer comprised between 0 and 5;

W is selected from the group consisting of O, $CO_2$, CONH and NHCONH;

f is selected from between 0 and 1;

J is H or an alkyl group $(CH_2)_q-CH_3$, wherein q is an integer comprised between 0 and 20;

$R_2$ and $R_3$, equal or different from each other, are selected from between R and $R_1$, wherein R and $R_1$ are defined as above, M is chosen from 2H and a metal selected from the group consisting of Zn, Mg, Pt, Pd, $Si(OR_7)_2$, $Ge(OR_7)_2$ and $AlOR_7$, wherein $R_7$ is chosen from between H and C1-C15 alkyl, and pharmaceutically acceptable salts thereof, with the exception of the following compounds:

a) compound of formula (I) wherein M is 2H, $R_1=R_3=H$, $R=R_2$ is a group of formula (II) in which s is 1, X is O, Y is $(CH_2)_3$, v is 1, Z is N, n=d=1, m is 0, and $R_4=R_5=H$; and b) compound of formula (I) wherein M is 2H, $R_1=R_3=H$, $R=R_2$ is a group of formula (II) in which s is 1, X is O, Y is $(CH_2)_3$, v is 1, Z is N, n=d=1, m is 0, $R_4$ and $R_5$ form with Z a phthalimido group; and irradiating the pathologically affected tissue with light of appropriate wavelength.

2. A method according to claim 1, wherein in the compound of general formula (I), the group R comprises at least one substituent bearing tertiary or quaternary nitrogen.

3. A method according to claim 1, wherein in the compound of general formula (I), the group

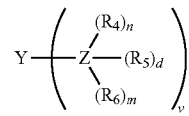

is selected from the group consisting of:

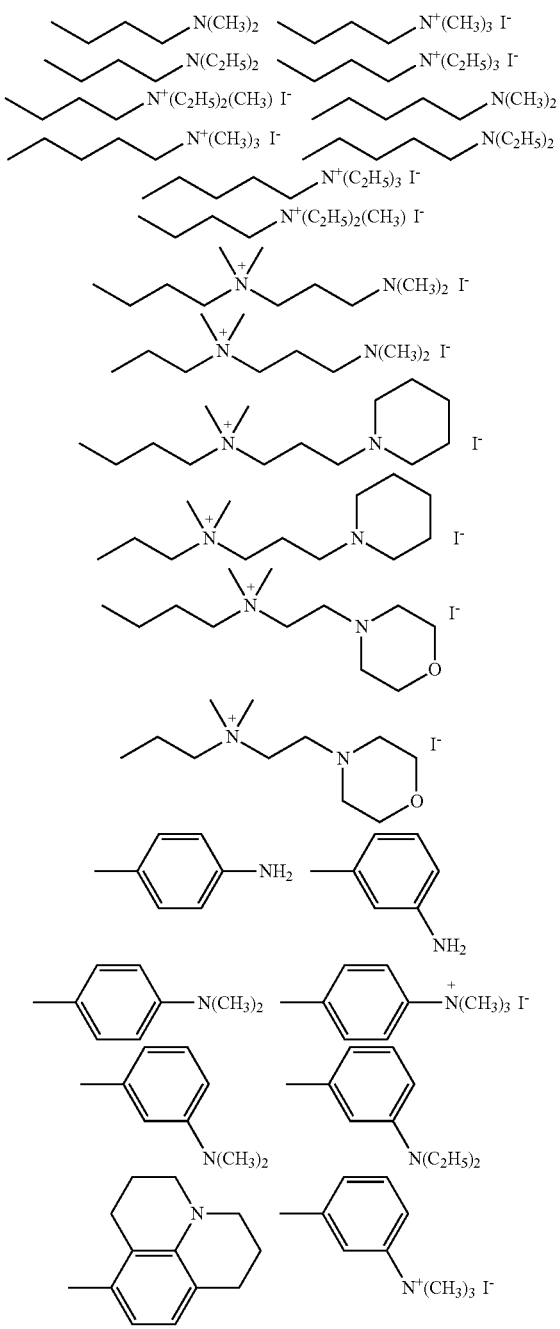

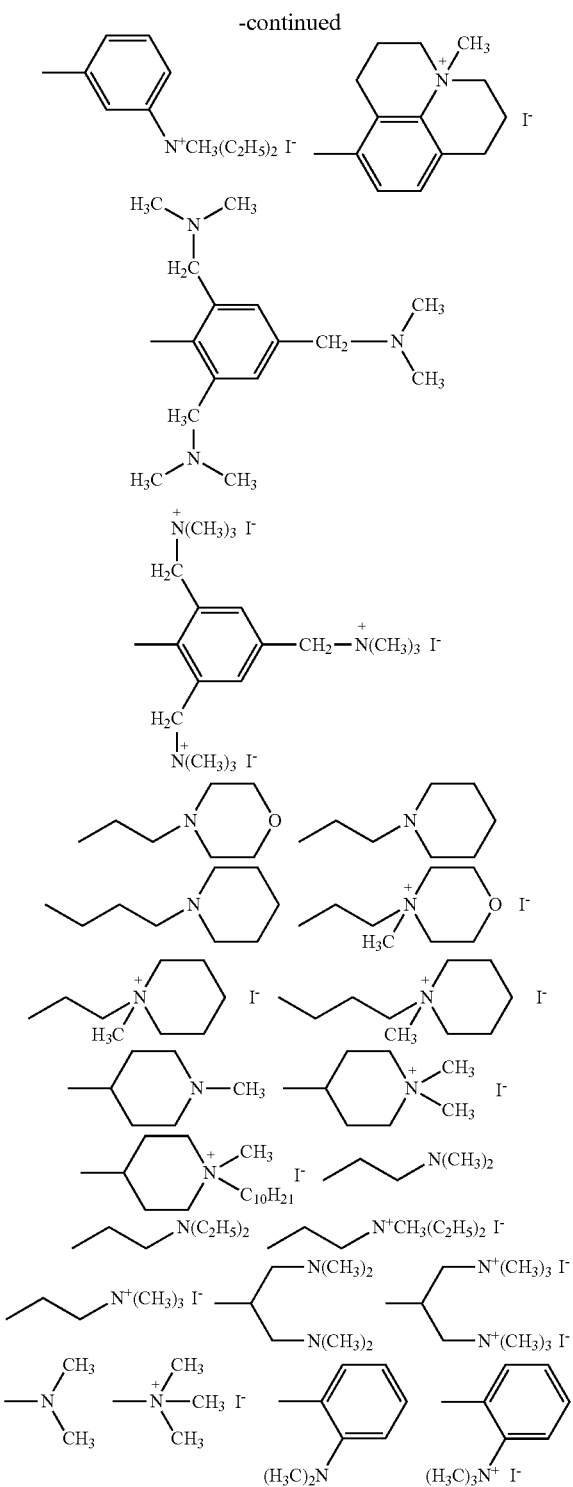

5,10,15-tris-[4-(2-N,N-dimethylaminoethoxy)-phenyl]-20-[(4-decyloxy)phenyl]porphyrinate zinc (II), 5,10,15-tris-{[4 -(N-methylpiperidin-4-yl)oxy]phenyl}-20-[(4-decyloxy)phenyl]porphyrin, 5,10,15-tris-{[4-(N,N-dimethylpiperidin-4-ium)oxy]phenyl}-20-[(4-decyloxy)phenyl]porphyrin triiodide, 5,10,15-tris-[3-(2-morpholin-4-ylethoxy)phenyl]-20-[(4-decyloxy)phenyl]porphyrin, 5,10,15-tris-{[3-(2-methylmorpholin-4-ium)ethoxy]phenyl}-20-[(4-decyloxy)phenyl]porphyrin triiodide, 5,10,15-tris-{4-[-4-(N,N-dimethylamino)phenoxy]phenyl}-20-[(4-decyloxy)phenyl]porphyrin, 5,10,15-tris-{4-[-4-(N,N,N-trimethylammonium)phenoxy]phenyl}-20-[(4-decyloxy)phenyl]porphyrin triiodide, 5,10,15-tris-{4-[3-(N,N-dimethylamino)phenyl]thiophenyl}-20-[(3-undecyloxy)phenyl]porphyrin, 5,10,15-tris-{4-[3-(N,N,N-trimethylammonium)phenyl]thiophenyl}-20-[(4-undecyloxy) phenyl]porphyrin triiodide, 5,10,15-tris-[3-(3-N,N-dimethylaminopropoxy)phenyl]-20-[(3-undecyloxy) phenyl]porphyrin, 5,10,15-tris-[3-(3-N,N,N-trimethylammoniumpropoxy)phenyl]-20-[(3-undecyloxy) phenyl]porphyrin triiodide, 5,10,15-tris-{4[4-(N,N-dimethylamino)butoxy]phenyl]-20-[(4-undecyloxy) phenyl]porphyrin, 5,10,15-tris-{4[4-(N,N,N-trimethylammonium)butoxy]phenyl}-20-[(4-undecyloxy) phenyl]porphyrin triiodide, 5-{4-{2,4,6-tris-[(dimethylamino)methyl]phenoxy}phenyl}-10,15,20-tris-[(4-decyloxy) phenyl]porphyrin, 5-{4-2,4,6-tris-[(trimethylammonium)methyl]phenoxy}phenyl}-10,15,20-tris-[(4-decyloxy) phenyl]porphyrin triiodide, 5-{3-[2-(dimethylamino)]-1-{[(dimethylamino)methyl]ethoxy}phenyl}-10,15,20-tris-[(3-decyloxy)phenyl]porphyrin, 5-{3-[2-(trimethylammonium)]-1-{[(trimethylammonium)methyl]ethoxy}phenyl}-10,15,20-tris-[(3-decyloxy)phenyl]porphyrin diiodide, 5,10,15-tris-{4-[3-(diethylamino)propoxy]phenyl}-20-[(4-decyloxy)phenyl]porphyrin, 5,10,15-tris-{4-[3-(trimethylammonium)propoxy]phenyl}-20-[(4-decyloxy)phenyl]porphyrin triiodide, 5,10,15-tris-[4-(2-aminoethoxy)phenyl]-20-[(4-decyloxy)phenyl]porphyrin, 5,10,15-tris-{[4-(2-trimethylammonium)ethoxy]phenyl}-20-[(4-decyloxy) phenyl]porphyrin triiodide, 5,10,15-tris-{{[4-(N,N,N-trimethylammonium)phenoxy]carbonyl}phenyl}-20-[(4-decyloxy) phenyl]porphyrin triiodide, 5-{4-{{2-(trimethylammonium)-1-[trimethylammonium)methyl]ethoxy}carbonyl}phenyl}-10,15,20-tris-[(3-decyloxy)phenyl]porphyrin diiodide, 5,15-bis-[3-(3-N,N,N-trimethylammoniumpropoxy)phenyl]porphyrin diiodide, 5,15-bis-[4-(2-piperidin-1-ylethoxy)phenyl]porphyrin, 5,15-bis-[4-(2-N-methylpiperidin-1-iumethoxy)phenyl]porphyrin diiodide, 4. A method according to claim 1, wherein the compound of general formula (I) is selected from the group consisting of:

5,10,15-tris-[4-(2-N,N,N-trimethylammoniumethoxy)-phenyl]-20-[(4-decyloxy)-phenyl]porphyrin triiodide, 5,10,15-tris-[4-(2-N,N,N-trimethylammoniumethoxy)-phenyl]-20-[(4-decyloxy)-phenyl]porphyrinate zinc (II) triiodide, 5,10,15-tris-[4-(2-N,N-dimethylaminoethoxy)phenyl]-20-[(4-decyloxy)phenyl]porphyrin], 5,15-bis-[4-(3-N,N-dimethylaminopropoxy)phenyl]-10,20-bis-[(3-decyloxy)phenyl]porphyrin,
5,15-bis-[4-[3-N,N,N-trimethylammoniumpropoxy)phenyl]-10,20-bis-[(3-decyloxy)phenyl]porphyrin diiodide,
5,15-bis 4-{[2-(N,N-dimethylamino)ethylthio]phenyl}porphyrin,
5,15-bis-{4-[2-(N,N,N-trimethylammonium)ethylthio]phenyl}porphyrin diiodide,
5,15-bis-{4-{2-[3-(trimethylammonium)phenoxy]ethoxy}phenyl}porphyrin diiodide,
5,15-bis-{4-{2-[3-(N,N,N-trimethylammonium)phenyl]-2-oxoethyl}-10,20-bis-[(3-decyloxy)phenyl]porphyrin diiodide,
5,15-bis-[3-(3-N,N,N-trimethylammoniumpropoxy)phenyl]porphyrinate zinc(II) diiodide,
5,15-bis-[3-(3-N,N-dimethylaminopropoxy)phenyl]porphyrinate zinc(II),
5,15-bis-[4-(4-N,N,N-trimethylammoniumphenoxy)phenyl]porphyrin diiodide,
5,15-bis-[4-(4-aminophenoxy)phenyl]porphyrin,
5,15-bis-[3-(4-N,N-dimethylaminophenoxy)phenyl]porphyrin,
5,15-bis-[3-(4-N,N,N-trimethylammoniumphenoxy)phenyl]porphyrin diiodide,
5,15-bis-[3-(4-N,N-dimethylaminophenyl)thiophenyl]porphyrin,
5,15-bis-[3-(4-N,N,N-trimethylammoniumthiophenoxy)phenyl]porphyrin diiodide,
5,15-bis-4-[3-(N,N-dimethylaminophenoxy)phenyl]-10,20-bis-[(4-decyloxy) phenyl]porphyrin,
5,15-bis-4-[3-(N,N,N-trimethylammoniumphenoxy)phenyl]-10,20-bis-[(4-decyloxy)phenyl]porphyrin diiodide,
5,10,15-tris-{4[4-(N,N-dimethylamino)butoxy]phenyl}-20-[(4-undecyloxy)phenyl]porphyrinate zinc(II),
5,10,15-tris-{4-[4-(N,N,N-trimethylammonium)butoxy]phenyl}-20-[(4-undecyloxy) phenyl]porphyrinate zinc (II) triiodide,
5,15-bis-[4-(2-piperidin-1-ylethoxy)phenyl]porphyrinate zinc(II), and
5,15-bis-[4-(2-N-methylpiperidin-1-iumethoxy)phenyl] porphyrinate zinc(II) diiodide.

5. A method according to claim 1, wherein the compound of general formula (I) is conjugated with a macromolecule selected from the group consisting of amino acids, polypeptides, proteins and polysaccharides.

6. A method according to claim 1, wherein in the compound of general formula (I), $R_6$ is selected from aliphatic groups, linear or branched, saturated or unsaturated, having from 1 to 5 carbon atoms, substituted with alkylamine or alkylammonium groups having alkyl chains comprising from 1 to 5 carbon atoms.

7. A method of treating infectious diseases of fungine or bacterial origin, comprising: administering to a patient having a pathologically affected tissue and in need of such a treatment an effective amount of at least a compound of general formula (I)

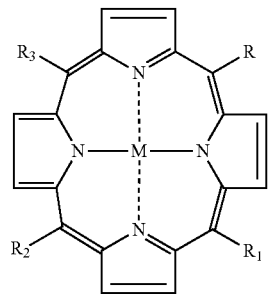

wherein
R is the following group of formula (II)

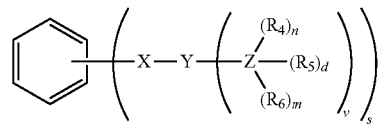

wherein
X is selected from the group consisting of O, S, $CH_2$, COO, $CH_2CO$, $O(CH_2)_2O$, $O(CH_2)_3O$ and N;
Z is selected from between N and $CH_2N$;
Y is selected from aliphatic groups, linear or branched, saturated or unsaturated, having from 1 to 10 carbon atoms, and phenyl or Y forms with Z a pyridine or substituted pyridine heterocycle, or an imidazole or substituted imidazole heterocycle;
$R_4$ and $R_5$, equal or different from each other, are selected from H and alkyl groups having from 1 to 3 carbon atoms, or they form with the Z group a pyridine or substituted pyridine heterocycle, or an imidazole or substituted imidazole heterocycle;
$R_6$ is selected from H and aliphatic groups, linear or branched, saturated or unsaturated, having from 1 to 5 carbon atoms, or comprising a saturated heterocycle selected from the group consisting of:
morpholine, piperidine, piperazine, pyrrolidine, and substituted forms thereof;
d, m, and n, equal of different from each other, are selected from 0 and 1;
v and s, equal or different from each other, are integers comprised between 1 and 3;
$R_1$ is selected from H and a group of formula (III)

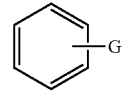

wherein
G is selected from H and P—$(CH_2)_l$—$(W)_{l'}$-J, wherein
P is selected from the group consisting of O, $CH_2$, $CO_2$, NHCONH and CONH;

l is an integer comprised between 0 and 5;

W is selected from the group consisting of O, CO$_2$, CONH and NHCONH;

f is selected from between 0 and 1;

J is H or an alkyl group (CH$_2$)$_q$—CH$_3$, wherein q is an integer comprised between 0 and 20;

R$_2$ and R$_3$, equal or different from each other, are selected from between R and R$_1$, wherein R and R$_1$ are defined as above, M is chosen from 2H and a metal selected from the group consisting of Zn, Mg, Pt, Pd, Si(OR$_7$)$_2$, Ge(OR$_7$)$_2$ and AlOR$_7$, wherein R$_7$ is chosen from between H and C1-C15 alkyl, and pharmaceutically acceptable salts thereof, with the exception of the following compounds:

a) compound of formula (I) wherein M is 2H, R$_1$=R$_3$=H, R=R$_2$ is a group of formula (II) in which s is 1, X is O, Y is (CH$_2$)$_3$, v is 1, Z is N, n=d=1, m is 0, and R$_4$=R$_5$=H; and b) compound of formula (I) wherein M is 2H, R$_1$=R$_3$=H, R=R$_2$ is a group of formula (II) in which s is 1, X is O, Y is (CH$_2$)$_3$, v is 1, Z is N, n=d=1, m is 0, R$_4$ and R$_5$ form with Z a phthalimido group; and irradiating the pathologically affected tissue with light of appropriate wavelength.

8. A method according to claim 7, wherein in the compound of general formula (I), the group

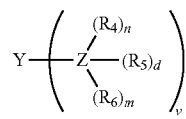

is selected from the group consisting of:

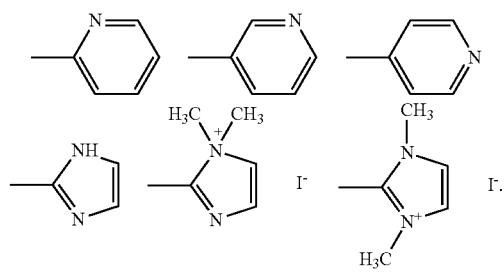

9. A method according to claim 7, wherein the compound of general formula (I) is conjugated with a macromolecule selected from the group consisting of amino acids, polypeptides, proteins and polysaccharides.

10. A method of treating infectious diseases of fungine or bacterial origin, comprising:

administering to a patient having a pathologically affected tissue and in need of such a treatment an effective amount of at least a compound of general formula (I)

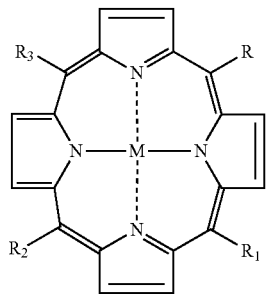

wherein
R is the following group of formula (II)

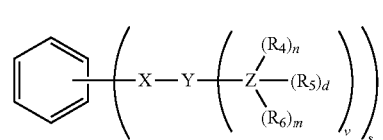

wherein
X is selected from the group consisting of O, S, CH$_2$, COO, CH$_2$CO, O(CH$_2$)$_2$O, O(CH$_2$)$_3$O and N;
wherein the group

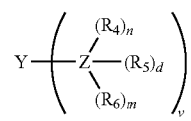

is selected from the group consisting of:

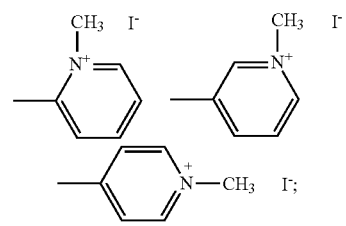

v and s, equal or different from each other, are integers comprised between 1 and 3;

R$_1$ is selected from H and a group of formula (III)

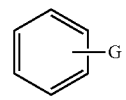

wherein
G is selected from H and P—(CH$_2$)$_l$—(W)$_f$-J, wherein
P is selected from the group consisting of O, CH$_2$, CO$_2$, NHCONH and CONH;
l is an integer comprised between 0 and 5;

W is selected from the group consisting of $O$, $CO_2$, $CONH$ and $NHCONH$;

f is selected from between 0 and 1;

J is H or an alkyl group $(CH_2)_q$—$CH_3$, wherein q is an integer comprised between 0 and 20;

$R_2$ and $R_3$, equal or different from each other, are selected from between R and $R_1$, wherein R and $R_1$ are defined as above, M is chosen from 2H and a metal selected from the group consisting of Zn, Mg, Pt, Pd, $Si(OR_7)_2$, $Ge(OR_7)_2$ and $AlOR_7$, wherein $R_7$ is chosen from between H and C1-C15 alkyl, and pharmaceutically acceptable salts thereof; and irradiating the pathologically affected tissue with light of appropriate wavelength.

* * * * *